US006214833B1

(12) United States Patent
Pellacini et al.

(10) Patent No.: US 6,214,833 B1
(45) Date of Patent: Apr. 10, 2001

(54) PYRIMIDINONE-1,3-OXATHIOLANE DERIVATIVES WITH ANTIVIRAL ACTIVITY

(75) Inventors: Franco Pellacini, Milan; Domenico Ungheri, Parabiago; Giovanna Schioppacassi, Milan, all of (IT); Jean-Louis Kraus; Michel Camplo, both of Marseilles (FR); Nicolas Mourier, Montpellier (FR); Jean-Claude Chermann, Marseilles (FR)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/381,635

(22) PCT Filed: Mar. 24, 1998

(86) PCT No.: PCT/EP98/01734
§ 371 Date: Jan. 31, 2000
§ 102(e) Date: Jan. 31, 2000

(87) PCT Pub. No.: WO98/43972
PCT Pub. Date: Oct. 8, 1998

(30) Foreign Application Priority Data

Mar. 28, 1997 (IT) .......................................... MI97A000737

(51) Int. Cl.$^7$ ........................ A61K 31/505; C07D 239/02
(52) U.S. Cl. ............................................. 514/274; 544/317
(58) Field of Search .............................. 514/274; 544/317

(56) References Cited

FOREIGN PATENT DOCUMENTS

| | | |
|---|---|---|
| 0382526 | 8/1990 | (EP) . |
| 0429436 | 5/1991 | (EP) . |
| 8801615 | 3/1988 | (WO) . |
| 9117159 | 11/1991 | (WO) . |
| 9214743 | 3/1992 | (WO) . |
| 9208717 | 5/1992 | (WO) . |
| 9414802 | 7/1994 | (WO) . |
| 9532200 | 11/1995 | (WO) . |
| 9618633 | 6/1996 | (WO) . |

OTHER PUBLICATIONS

A.S. Charvet et al., "Inhibition of Human Immunodefiency Virus Type 1 Replication by Phosphonoformate—and Phosphonoacetate–2', 3'–Dideoxy–3'–Thiacytidine Conjugates", *J. Med. Chem.*, vol. 37, No. 14, 1994, pp. 2216–2223.

M. Camplo et al., "Synthesis and Comparative anti–HIV Activities of New Acetylated 2' 3'–Dideoxy–3'–Thiacytidine Analogues", *Europ. J. Med. Chem. Ther.*, vol. 29, 1994, pp. 357–362.

A.Charvet at al. "Inhib. of Hunam Imm. Vir . . . " J. Med. Chem. 37/14,2216–23, Jul. 1994.*

M.Camplo et al. "Synt.&Comp.antiHIV Acti.""Eur.J.Med.Chem.Ther." 29,357–62, Jul. 1994.*

* cited by examiner

*Primary Examiner*—Mukund J. Shah
*Assistant Examiner*—Sudhaker B. Patel
(74) *Attorney, Agent, or Firm*—Arent Fox Kintner Plotkin Kahn PLLC

(57) ABSTRACT

Compounds of formula (I) wherein $R_a$ and $R_b$, the same or different, are hydrogen atoms, acyl groups deriving from a lower carboxylic acid or chains of formula (a) useful as reverse transcriptase inhibitors antiviral activity are described.

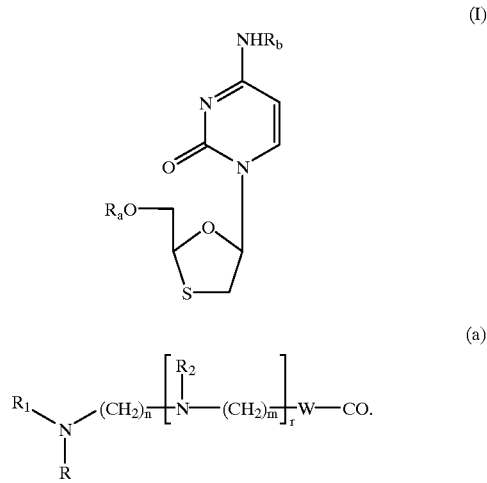

12 Claims, No Drawings

PYRIMIDINONE-1,3-OXATHIOLANE DERIVATIVES WITH ANTIVIRAL ACTIVITY

The present invention relates to antiviral nucleosides and, more particularly, relates to 1,3-oxathiolane derivatives endowed with reverse transcriptase inhibitory activity Since the discovery of HIV virus, responsible for AIDS, remarkable efforts have been made in the attempt of identifying an effective therapy.

Some nucleoside derivatives, such as zidovudine, zalcitabine, didanosine and stavudine (USP Dictionary of USAN and International Drug Names, 1997, pages 774, 772, 228 and 669 respectively), have become of clinical use, each other sometimes in association.

All these drugs act as reverse transcriptase inhibitors (RT-inhibitors).

In fact, reverse transcriptase is an enzyme involved in the intracellular replication of the virus because it catalyses the DNA transcription from the viral RNA.

Therefore, the RT-inhibitors act in a very early vital stage of the viral replication and this is the reason of their remarkable therapeutic interest.

On the other hand, the prolonged use of RT-inhibitors used up to now in therapy is practically impossible because of the appearance of resistance, side-effects and toxic effects mainly connected with their low selectivity.

Very recently, (2R-cis)-4-amino-1-(2-hydroxymethyl-1,3-oxathiolan-5-yl)-2(1H)-pyrimidinone, better known with the common name lamivudine (USP Dictionary of USAN and International Drug Names, 1997, page 398), a compound described in the International patent application no. WO 91/17159 (IAF Biochem International Inc.) as more potent and less toxic antiviral than zidovudine, zalcitabine, didanosine and stavudine has entered the clinical use.

Lamivudine is the levorotatory enantiomer (2R,5S) of the compound known with the code BCH-189 described in the European patent application no. 0 382 526 (IAF Biochem International Inc.).

Notwithstanding the progress obtained in these last years in the treatment of AIDS, the disease still has a huge medical and social relevance for its extreme seriousness and for its fast spread.

Therefore, there is still a very high need of new drugs endowed with an always greater efficacy and with an always minor toxicity, then particularly suitable for prolonged therapies too.

The International patent application no. WO 95/32200 (Laboratoire Laphal) describes derivatives of lamivudine and of BCH-189 characterised by the presence of an acyl or arylalkoyl group deriving from a mono or bicyclic nitrogen containing heterocycle, as substituent of the amino group.

We have now found that by introducing a nitrogen containing chain of formula

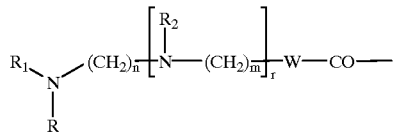

wherein
R is a hydrogen atom, a linear or branched $C_1$–$C_6$ alkyl group, a $C_3$–$C_7$ cycloalkyl group or a group selected among

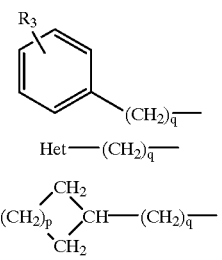

wherein q is an integer from 1 to 3; p is an integer from 1 to 4; Het is a 5 or 6 member heterocycle containing 1 or 2 heteroatoms selected among oxygen, nitrogen and sulfur and $R_3$ is a hydrogen or halogen atom, a trifluoromethyl group or a $C_1$–$C_3$ alkoxy group;

$R_1$ and $R_2$, the same or different, are hydrogen atoms, phenylalkoxycarbonyl groups having from 1 to 3 carbon atoms in the alkoxy moiety, $C_2$–$C_6$ alkoxycarbonyl groups or $C_2$–$C_6$ alkylcarbonyl groups;

W is a single bond, an oxygen atom or a —CH(Alk)— group wherein Alk is a linear or branched $C_1$–$C_3$ alkyl group;

r is 0 or 1;
n=x when r is 0
n=y when r is 1;
x is an integer from 1 to 6;
y is an integer from 2 to 7;
m is an integer from 2 to 7;

onto a function of lamivudine which can be acylated, the antiviral activity of lamivudine is remarkably strengthened.

Therefore, object of the present invention are compounds of formula

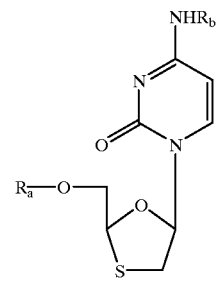

(I)

wherein $R_a$ and $R_b$, the same or different, are hydrogen atoms, acyl groups deriving from a lower carboxylic acid or chains of formula

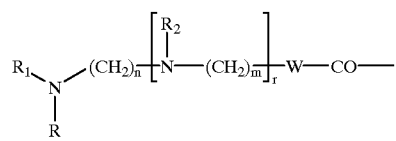

wherein

R is a hydrogen atom, a linear or branched $C_1$–$C_6$ alkyl group, a $C_3$–$C_7$ cycloalkyl group or a group selected among

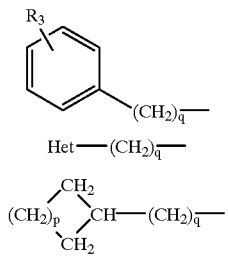

wherein q is an integer from 1 to 3; p is an integer from 1 to 4; Het is a 5 or 6 member heterocycle containing 1 or 2 heteroatoms selected among oxygen, nitrogen and sulfur and $R_3$ is a hydrogen or halogen atom, a trifluoromethyl group or a $C_1$–$C_3$ alkoxy group;

$R_1$ and $R_2$, the same or different, are a hydrogen atom, a phenylalkoxycarbonyl group having from 1 to 3 carbon atoms in the alkoxy moiety, a $C_2$–$C_6$ alkoxycarbonyl group or a $C_2$–$C_6$ alkylcarbonyl group;

W is a single bond, an oxygen atom or a —CH(Alk)— group wherein Alk is a linear or branched $C_1$–$C_3$ alkyl group;

r is 0 or 1;

n=x when r is 0 n=y when r is 1;

x is an integer from 1 to 6, y is an integer from 2 to 7;

m is an integer from 2 to 7;

provided that at least one of $R_a$ and $R_b$ is different from a hydrogen atom or from an acyl group deriving from a lower carboxylic acid; tautomeric forms and pharmaceutically acceptable salts thereof.

The compounds of formula I are lamivudine derivatives (prodrugs) which release lamivudine into the organism but are endowed with antiviral activity, as reverse transcriptase inhibitors, more potent than lamivudine on lymphocytes and, particularly, on macrophages.

Notwithstanding in the literature, as already reported, the term lamivudine more commonly refers to the levorotatory enantiomer (2R-cis) of 4-amino-1-(2-hydroxymethyl-1,3-oxathiolan-5-yl)-2(1H)-pyrimidinone, while the corresponding racemate is referred to as the code BCH- 189, for the sake of simplicity in the present context, if not otherwise specified, the term lamivudine refers to the compound of formula

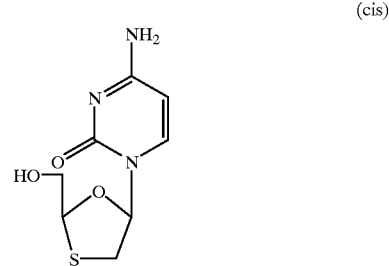

(cis)

in the form of stereoisomeric mixture as well as in the form of one of the possible isomers thereof.

The compounds of formula I, object of the present invention, can have a single chain, bound to the OH function or to the $NH_2$ function of lamivudine, or two chains bound to the OH function and to the $NH_2$ function of lamivudine. Specific examples of compounds of formula I are:

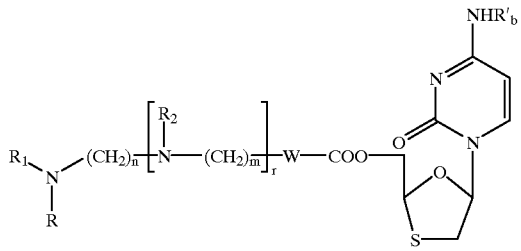

(I-A)

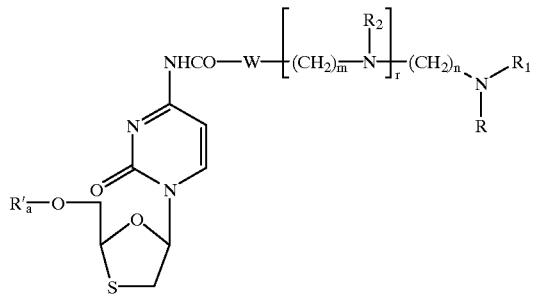

(I-B)

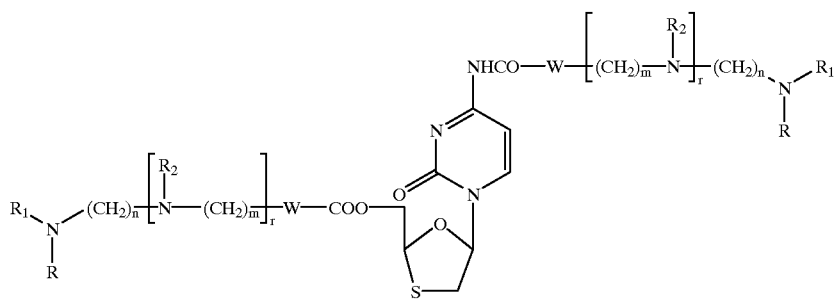

wherein R, $R_1$, $R_2$, W, n, m and r have the already reported meanings; $R'_a$ and $R'_b$ are hydrogen atoms or an acyl group deriving from a lower carboxylic acid.

In the present description, when not otherwise specified, the term linear or branched $C_1$–$C_6$ alkyl refers to a group selected among methyl, ethyl, propyl, isopropyl, butyl, sec-butyl, isobutyl, tert-butyl, pentyl, neopentyl, isopentyl, tert-pentyl, sec-pentyl, hexyl and isohexyl; the term $C_2$–$C_7$ cycloalkyl refers to a group selected among cyclopropyl, cyclobutyl, cyclopentyl, cyclohexyl and cycloeptyl; the term $C_1$–$C_3$ alkoxy refers to a group selected among methoxy, ethoxy, propoxy and isopropoxy; the term $C_2$–$C_6$ alkoxycarbonyl refers to a group selected among methoxycarbonyl, ethoxycarbonyl, propoxycarbonyl, isopropoxycarbonyl, butoxycarbonyl, isobutoxycarbonyl, tert-butoxycarbonyl (also referred to as BOC), sec-butoxycarbonyl and pentoxycarbonyl; the term $C_2$–$C_6$ alkylcarbonyl refers to a group selected among acetyl, propionyl, butyryl, isobutyryl, valeryl, isovaleryl, pivaloyl and hexanoyl; the term acyl deriving from a lower carboxylic acid refers to a group selected among acetyl, propionyl, butyryl and isobutyryl, the term 5 or 6 member heterocycle containing 1 or 2 heteroatoms selected among oxygen, nitrogen and sulphur refers to a heterocycle selected among thiophene, furan, pyrane, pyrrole, imidazole, pyrazole, isothiazole, thiazole, isoxazole, oxazole, pyridine, pyrazine, pyrimidine and pyridazine, optionally benzocondensed.

A class of preferred compounds of formula I is represented by the compounds having, the (2R,5S) configuration of lamivudine.

Another class of preferred compounds is represented by the compounds of formula I-A.

Within this class, preferred compounds are the compounds wherein $R_1$ and $R_2$ are different from hydrogen and, more preferably, are $C_2$–$C_6$ alkoxycarbonyl groups such as, for example, ethoxycarbonyl or tert-butoxycarbonyl groups.

Still more preferred are the compounds of formula I-A wherein $R_1$ and $R_2$ are different from hydrogen and R is a group of formula

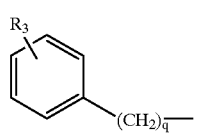

wherein $R_3$ and q have the already reported meanings.

Another class of particularly interesting compounds is represented by the compounds of formula I wherein R is a group of formula

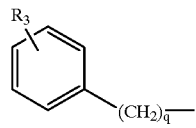

wherein q is 1 and $R_3$ has the already reported meanings.

The compounds of formula I wherein W is a single bond; R is a group of formula

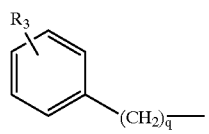

in which q is 1;
$R_3$ is a hydrogen atom or a trifluoromethyl group are particularly preferred.

Still more preferred are the compounds of formula I wherein W is a single bond; R is a group of formula

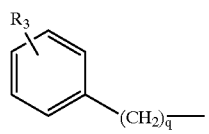

q is 1;
$R_3$ is a hydrogen atom or a trifluoromethyl group;
n is an integer from 4 to 6 and m is selected among 4 and 5.

The preparation of the compounds of formula I, object of the present invention, can be carried out by acylation according to conventional techniques.

In particular, lamivudine is acylated by reaction with a compound of formula

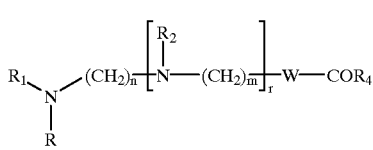

wherein R, $R_1$, $R_2$, n, m and W have the already reported meanings and $R_4$ is an OH group or a suitable leaving group when W is different from oxygen or $R_4$ is a suitable leaving group when W is oxygen.

In general, when the acylation is carried out by directly using a compound of formula II wherein $R_4$ is OH, also a condensation agent such as dicyclohexylcarbodiimide (DDC), (benzotriazol-1-yloxy)tris(dimethylamino) phosphonium hexafluorophosphate (BOP), carbonyl-1,1'-diimidazole (CDI) or pivaloyl chloride/LiCl is used.

The intermediate of formula II is generally used in a protected form.

The term protected from has to be intended in its broadest meaning. In fact, protected intermediate refers to an intermediate already bearing the $R_1$ and $R_2$ functions foreseen for the final compound on the amino groups as well as bearing $R_1$ and $R_2$ functions which will be removed to obtain the compounds of formula I wherein $R_1$ and $R_2$ are hydrogen atoms or to obtain, after further finctionalization, the compounds of formula I wherein $R_1$ and $R_2$ are different from hydrogen and particularly are acyl groups.

The direct acylation of lamivudine with a compound of formula II, according to what already reported, leads to the obtainment of a mixture of compounds of formula I-A, I-B and I-C which can be then separated with conventional techniques, for example by chromatography.

By suitably changing the operative conditions it will be possible to selectively acylate only one of the OH or $NH_2$ lamivudine functions, so obtaining the compounds of formula I-A or I-B.

For the preparation of the compounds of formula I-A, for example, the selective protection of the $NH_2$ function of lamivudine, the acylation with a compound of formula II and optionally the removal of the protecting group can be carried out. The selective protection of the $NH_2$ function of lamivudine can be carried out by using acyl groups, preferably acetyl, or through the formation of imines.

In this last case, after acylation of the OH group with a suitable compound of formula II according to what already reported, the protecting group will be removed by treatment with diluted acids.

Similarly, for the preparation of the compounds of formula I-B the OH function of lamivudine can be selectively protected.

Examples of suitable protecting groups of the OH function are silyl derivatives, such as tert-butyldimethylsilyl, tert-butyidiphenylsilyl or trimethylsilyl, which can then be removed by treatment with diluted acids or with tetrabutylammoniumfluoride.

The compounds of formula II wherein r=0 are known or can be prepared with known methods.

For example, the compounds of formula II wherein r=0, W is different from oxygen, R and $R_1$ are hydrogen atoms are generally commercially available.

The preparation of compounds of formula II wherein r=0, W is different from oxygen and one or both R and $R_1$ are different from hydrogen is preferably carried out starting from the corresponding aminoalcohols of formula

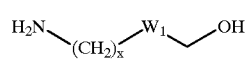

(III)

wherein x has the already reported meanings and $W_1$ is a single bond or a group —CH(Alk)— wherein Alk is a linear or branched $C_1$–$C_3$ alkyl group;

a) by direct alkylation or by reaction with a suitable aldehyde followed by reduction of the imine and/or b) by acylation with a suitable acylating agent so obtaining the compounds of formula

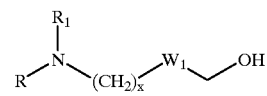

(IV)

wherein x and $W_1$ have the already reported meanings, one or both R and $R_1$ are different from hydrogen.

The corresponding compounds of formula II wherein r=0 can be then obtained by the aminoalcohols of formula III or IV.

For example, by oxidation of the alcoholic function according to conventional techniques the compounds of formula

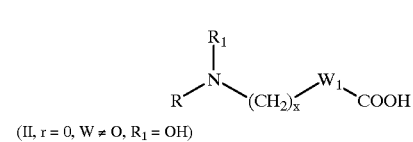

(IIa)

(II, r = 0, W ≠ O, $R_1$ = OH)

wherein R, $R_1$, $W_1$ and x have the already reported meanings will be obtained.

The selected oxidation conditions will depend on the eventual presence of other oxidizable functions in the molecule.

Preferably, the oxidation is carried out by using pyridinium dichromate or TEMPO/NaOCl as oxidising agents.

Instead, the compounds of formula II wherein r=0 and W is an oxygen atom are prepared from the compounds of formula

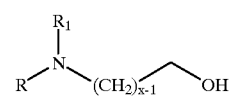

(IVa)

wherein R, $R_1$ and x have the already reported meanings;

by reaction with a suitable carbonyl derivative of formula $(R_4)_2CO$ wherein $R_4$ is a suitable leaving group, preferably an imidazol-1-yl group, so obtaining the compounds of formula

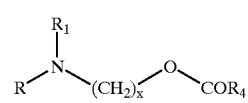

(IIb)

(II, r = 0, W = O)

wherein R, $R_1$, $R_4$ and x have the already reported meanings.

The compounds of formula II wherein r=1 are prepared starting from the compounds of formula III or IV wherein $W_1$ is a single bond, according to the following synthetic scheme.

Scheme 1

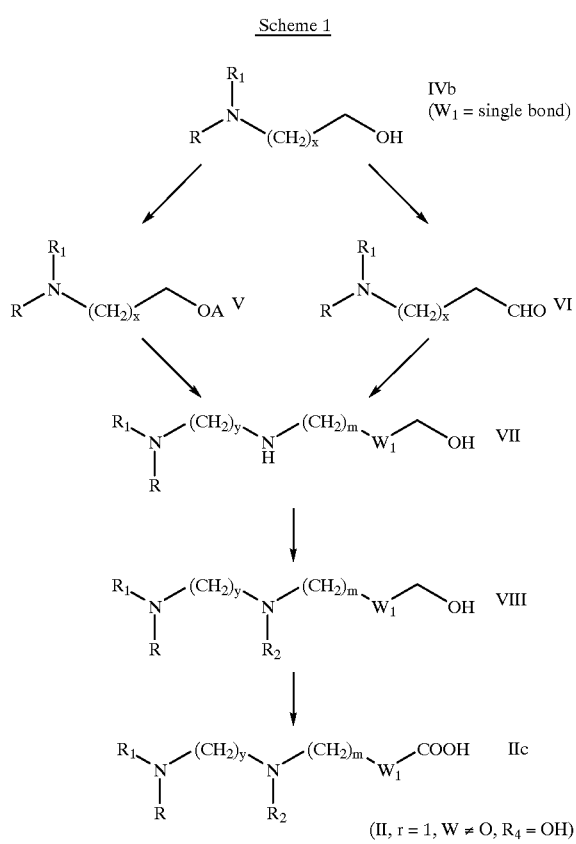

wherein R, R$_1$, R$_2$, x, y, m and W$_1$ have the already reported meanings and A is an activating group, preferably mesyl or a tosyl.

The aminoalcohol (IVb) is suitably activated to be condensed with an aminoalcohol of formula III.

The activation can be carried out by reaction with a suitable sulfonyl halide, for example tosyl or mesyl chloride, obtaining the corresponding compound of formula V which by condensation with the aminoalcohol III, directly gives the intermediate VII. Alternatively, the activation is carried out by oxidation to the corresponding aldehyde VI which is first condensed with the aminoalcohol III giving an imine and which is then directly reduced obtaining the compound VII.

The eventual protection of the intermediate VII followed by the oxidation according to what already reported enables to obtain the compounds of formula IIc.

Also the compounds of formula II wherein r=1 and W is an oxygen atom are prepared from the corresponding compounds of formula

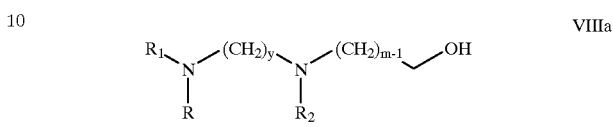

wherein R, R$_1$, R$_2$, y and m have the already reported meanings;
in a very similar way to that reported for obtaining the compounds of formula IIb, so giving the compounds of formula

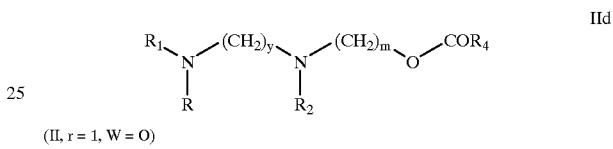

wherein R, R$_1$, R$_2$, R$_4$, y and m have the already reported meanings.

The synthesis of the compounds of formula I, object of the present invention, is illustrated in more details in the following scheme, with particular reference to the preparation of the compounds of formula I-A wherein W is a simple bond and R is a group of formula

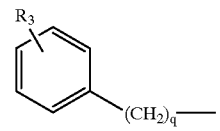

wherein R$_3$ and q have the already reported meanings.

Scheme 2

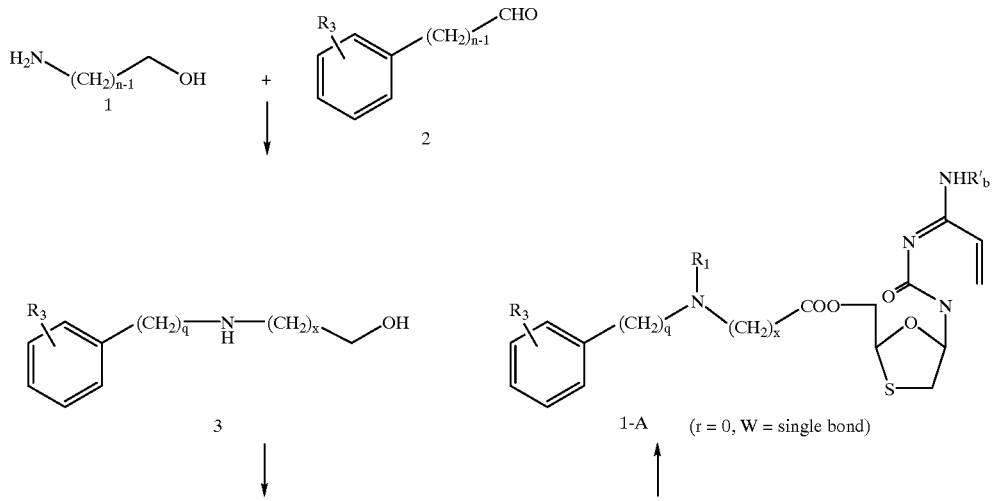

-continued

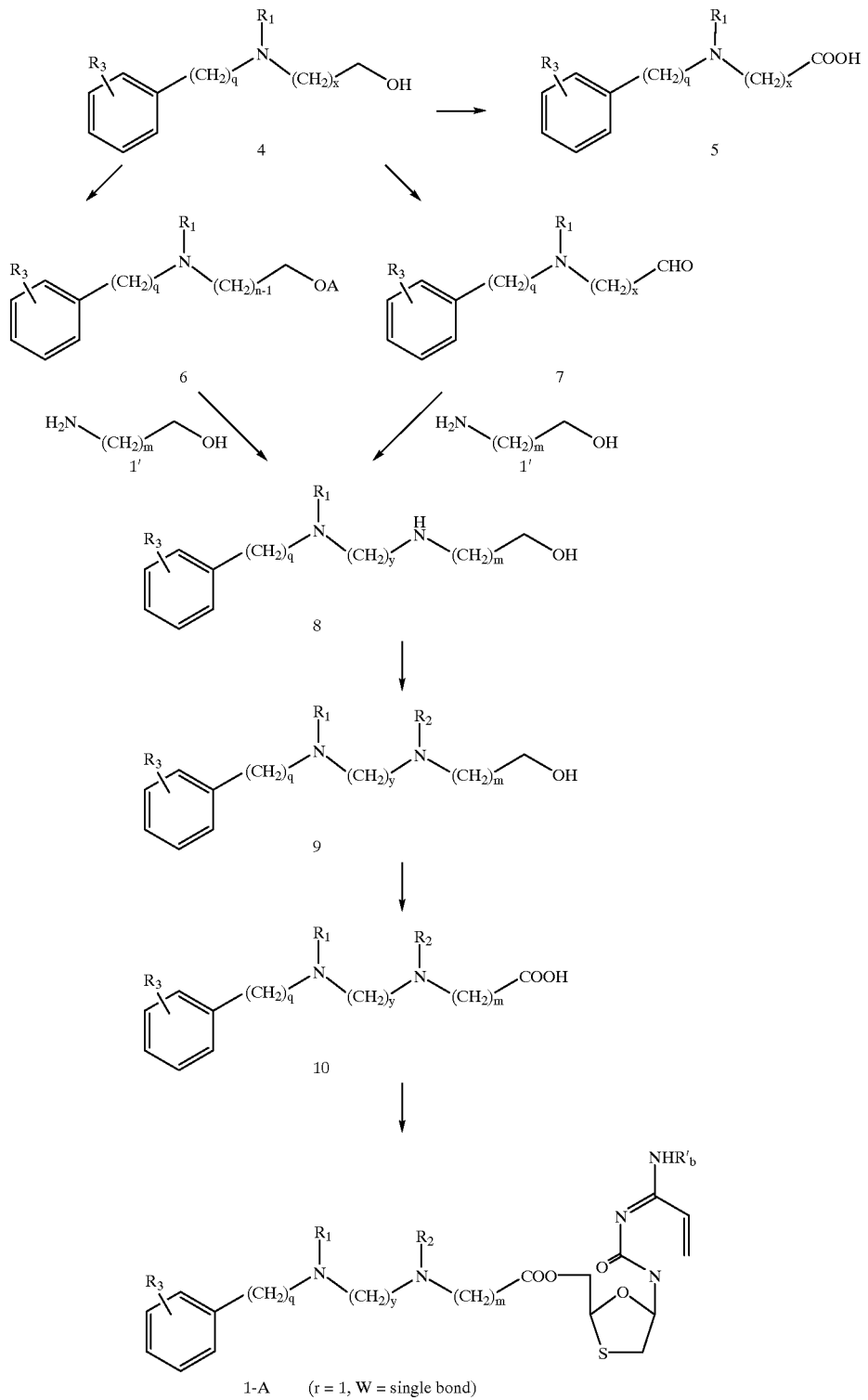

1-A  (r = 1, W = single bond)

wherein $R_1$, $R_2$, $R_3$, $R'_b$, q, x, y, m and n have the already reported meanings.

The condensation of the aminoalcohol 1 with the aldehyde 2, followed by the reduction of the intermediate imine carried out direct in situ or after isolation, gives the alcohol 3 which is protected, preferably by functionalization with an alkoxycarbonyl or phenylalkoxycarbonyl group, to obtain intermediate 4.

The intermediate 4 is oxidised to the corresponding carboxylic derivative 5 which can be used for the acylation of the optionally protected lamivudine.

Alternatively, the protecting group $R_1$ of compound 5 can be removed according to conventional techniques and the resultant compound of formula 5 wherein $R_1$=H can be acylated with acyl halides, to obtain the compounds of formula 5 wherein $R_1$ is an acyl group.

The intermediate 4 can also be used for the preparation of the compounds of formula 10 (II, r=1).

In such a case, the intermediate 4 is suitably activated (compound 6 or 7) according to what already reported to be condensed with an aminoalcohol of formula 1'.

The resultant compound 8, after protection of the secondary amino function is oxidised.

Then, the compound 10 is used in a very similar way to that already described for the compound 5 for direct acylating lamivudine or for obtaining the corresponding compounds of formula 10 wherein $R_1$ and $R_2$ are acyl groups.

Alternatively, the compounds of formula 10 can also be prepared by oxidation of the corresponding compounds of formula 9 wherein $R_1$=$R_2$=H, described in the International patent application no. WO 96/18633 in the name of the same Applicant, so obtaining the compounds of formula 10 wherein $R_1$=$R_2$ =H or by functionalization of the amino functions and oxidation, so obtaining the compounds of formula 10 wherein $R_1$ and $R_2$ are different from hydrogen.

The compounds of formula I, object of the present invention, are lamivudine derivatives endowed with a remarkable antiviral activity on limphocitic cells and in particular on macrophagic cells as reverse transcriptase inhibitors.

It is worth underlining that the antiviral activity of the compounds of formula I is generally higher than that of lamivudine, in some cases up to 1000 times more potent. Furthermore, the compounds object of the present invention are also active on HIV strains resistant to the best known RT-inhibitors.

The compounds of formula I, object of the present invention, differ from lamivudine for a higher selectivity index toward macrophages.

The so significantly higher activity and selectivity data have led to make the hypothesis that the compounds of formula I, object of the present invention, besides being lamivudine pro-drugs are also involved in a mechanism of action, for example a transport through the cell membranes of lymphocytes and of macrophages, which there is not in the case of lamivudine.

It is worth underlining that from a therapeutic viewpoint, the potent antiviral activity as well as the remarkable selectivity represent an important advantage of the compounds object of the present invention in comparison with the RT-inhibitors class, and in particular, with lamivudine.

In fact, it is known that macrophages are extremely important and, at the same time, difficulty reachable targets in the treatment of HIV infections.

It is also known that macrophages have a role of "reservoir" for HIV virus in humans (J. Embretson et al., Nature, vol. 362, pages 359–362, 1993).

The possibility of targetting the macrophages with a compound having a so potent antiviral activity enables to act effectively on the virus also during the asymphomatic phase of the disease when the virus is still silent and stored into the macrophages.

The antiviral activity of the compounds of formula I, object of the present invention, was evaluated on the MT4 human lymphocytes infected by HIV-1 BRU strain and on fresh human macrophages infected by the macrophage-trophic HIV-1 PAR strain.

Both kinds of experiment were carried out following conventionally used methods for the evaluation of reverse transcriptase inhibitors and are predictive of the in vivo anti-HIV activity.

For the use in therapy, the compounds of formula I can be administered by oral or parenteral route with suitable pharmaceutical forms.

For the parenteral administration the compounds of formula I can, for example, be used as aqueous solutions or suspensions.

For the oral administration the compounds of formula I can be formulated in solid compositions, such as for example tablets, capsules, granulates, or in liquid compositions, such as solutions and suspensions.

Therefore, a further object of the present invention are pharmaceutical compositions containing one or more compounds of formula I in admixture with a pharmaceutically acceptable carrier.

The pharmaceutically acceptable carrier will depend on the selected kind of composition and will be made by one or more excipients suitable for the pharmaceutical use such as, for example, disintregants, diluents, surfacting agents, colouring agents, flavouring agents, buffering agents, preservatives, etcetera.

The pharmaceutical compositions object of the present invention can also contain one or more compounds of formula I in association with one or more known antivirals such as zidovudine, zalcitabine, didanosine and stavudine.

The therapeutic dose or the compounds of formula I will chance depending on the administration route and on the patient condition but will be generally from 50 mg and 300 mg, divided into one or two daily administrations (bis in diem=b.i.d.).

In order to better illustrate the present invention the following examples are now given.

Abbreviations and symbols used in the examples

| Starting compounds: | |
| --- | --- |
| 1a = 1'a | 6-aminohexan-1-ol |
| 1b = 1'b | 5-aminopentan-1-ol |
| 1c = 1'c | 4-aminobutan-1-ol |
| 1d = 1'd | 3-aminopropan-1-ol |
| 1e = 1'e | 2-aminoethanol |
| 2a | benzaldheyde |
| 2b | 3-trifluoromethylbenzaldheyde |
| 2c | 2-trifluoromethylbenzaldheyde |
| 2d | 4-methoxybenzaldheyde |
| Reagents: | |
| $BOC_2O$ | di-tert-butyl-dicarbonate |
| TEMPO | 2,2,6,6-tetramethyl-1-piperidinyloxy free radical |
| Aliquat ® | tricaprilylmethylammonium chloride |
| TsCl | tosyl chloride |
| $Et_3N$ | triethylamine |
| CDI | carbonyl-1,1'-diimidazole |
| BOP | (benzotriazol-1-yloxy)tris(dimethylamino)fosfonium hexafluorofosfate |
| Solvents: | |
| DMF | N.N-dimethylformamide |
| $Et_2O$ | ethyl ether |
| AcOEt | ethyl acetate |
| Others: | |
| Ts | tosyl |
| BOC | tert-butoxycarbonyl |
| Ac | acetyl |
| Piv | pivaloyl |
| Bz | benzyl |
| Ph | fenyl |
| Et | ethyl |
| t.Bu | tert-butyl |

Part A—Synthesis of the Side Chains

EXAMPLE 1A

Preparation of the compounds of formula 3

Method A

To 1 equivalent of aminoalcohol 1 dissolved in water 1.1 equivalents of aldehyde 2 dissolved in $Et_2O$ were added. The mixture was kept under stirring overnight at room temperature. After extraction with $Et_2O$, the organic phase was dried on $Na_2SO_4$ and evaporated to yield an oily residue. The resultant imine, characterised by TLC, was used in the subsequent step without further purifications.

A solution of $NaBH_4$ in ethanol at 0° C. was added to 1 equivalent of the resultant crude imine dissolved in ethanol. The mixture was kept under stirring for 2 hours at 0° C. and for further 2 hours at room temperature. After evaporation of ethanol, the residue was washed with water and extracted with AcOEt. The organic phase was dried on $Na_2SO_4$ and evaporated. The residue was purified by column chromatography.

Method B

To 1 equivalent of aminoalcohol 1 in ethanol, in the presence of 3 Å molecular sieves, 1 equivalent of aldehyde 2 was added and the mixture was kept under stirring fro 2.5 hours. After filtration of the molecular sieves, $NaBH_4$ was added portionwise to the resultant solution, under stirring under nitrogen atmosphere and by keeping the temperature at 15–20° C. After 1.5 hours, the solvent was evaporated under reduced pressure and the residue was taken up with water.

After extraction with $Et_2O$, the organic phases were washed with a solution of NaCl and dried on $Na_2SO_4$.

The solvent was evaporated under reduced pressure.

The following compounds of formula 3 were obtained:

6-Phenylmethylamino-hexan-1-ol (3a)

($R_3$=H, q=1, x=5) from 1a and 2a (methods A and B).
Rf=0.2 ($CH_2Cl_2$:$CH_3OH$=9:1)
$^1$H-NMR (200 MHz, $CDCl_3$): 7.35–7.18 (m, 5H, Ar); 3.75 (s, 2H, C$\underline{H}_2$ —Ar); 3.60 (t, 2H, C$\underline{H}_2$OH); 2.60 (t, 2H, N—$CH_2$); 1.65 (bs, 1H, OH); 1.60–1.30 [m, 8H, $CH_2$—(C$\underline{H}_2$)$_4$—$CH_2$].

6-(3-Trifluoromethylphenyl)methylamino-hexan-1-ol (3b)

($R_3$=3-$CF_3$, q=1, x=5) from 1a and 2b (method A).
Rf=0.35 ($CH_2Cl_2$:$CH_3OH$=9:1)

6-(2-Trifluoromethylphenyl)methylamino-hexan-1-ol (3c)

($R_3$=2-$CF_3$, q=1, x=5) from 1a and 2c (method A).
Rf=0.30 ($CH_2Cl_2$:$CH_3OH$=9:1)

5-Phenylmethylamino-pentan-1-ol (3d)

($R_3$=H, q=1, x=4) from 1b and 2a (methods A and B).
Rf=0.40 ($CH_2Cl_2$:$CH_3OH$=8.5:1.5)
$^1$H-NMR (200 MHz, $CDCl_3$): 7.35–7.18 (m, 5H, Ar); 3.73 (s, 2H, C$\underline{H}_2$ —Ar); 3.55 (t, 2H, C$\underline{H}_2$OH); 2.61 (t, 2H, N—$CH_2$); 2.00 (bs, 1H, OH); 1.60–1.30 [m, 6H, $CH_2$—(C$\underline{H}_2$)$_3$—$CH_2$].

4-Phenylmethylamino-butan-1-ol (3e)

($R_3$=H, q=1, x=3) from 1c and 2a (method B).
$^1$H-NMR (200 MHz, $CDCl_3$): 7.35–7.18 (m, 5H, Ar); 3.73 (s, 2H, C$\underline{H}_2$ —Ar); 3.57–3.52 (m, 2H, C$\underline{H}_2$OH); 3.50 (bs, 1H, OH); 2.70–2.62 (m, 2H, N—$CH_2$); 1.71–1.53 [m, 4H, $CH_2$—(C$\underline{H}_2$)$_2$—$CH_2$].

3-Phenylmethylamino-propan-1-ol (3f)

($R_3$=H, q=1, x=2) from 1d and 2a (method B).
$^1$H-NMR (200 MHz, $CDCl_3$): 7.37–7.20 (m, 5H, Ar); 3.33–3.28 (m, 2H, C$\underline{H}_2$OH); 3.28 (s, 2H, C$\underline{H}_2$ —Ar); 2.45 (bs, 1H, OH); 2.43–2.38 (m, 2H, N—$CH_2$); 1.78–1.65 [m, 2H, $CH_2$—C$\underline{H}_2$—$CH_2$].

EXAMPLE 2A

Preparation of the compounds of formula 4

Method A

To 1 equivalent of compound of formula 3, prepared as described in example 1A, dissolved in $CH_2Cl_2$, 1.1 equivalents of $BOC_2O$ in $CH_2Cl_2$ were added at 0° C. The mixture was kept under stirring for 3 hours at 0° C. and then for further 4 hours at room temperature. After evaporation of the solvent, the isolated residue was used without further purification.

Method B $BOC_2O$ dissolved into a little dioxane was added dropwise to 1 equivalent of compound of formula 3, prepared as described in example 1A, dissolved in a 2:1 dioxane-water mixture, under stirring at 0° C.

The reaction mixture was brought to room temperature and after 2.5 hours the solution was concentrated by evaporating dioxane under reduced pressure.

After extraction with AcOEt, drying on $Na_2SO_4$ and filtration, the solvent was evaporated under reduced pressure.

The crude was purified by flash chromatography on silica.

The following compounds of formula 4 were obtained:

6-(N-tert-Butoxycarbonyl-N-phenylmethylamino)-hexan-1-ol (4a)

($R_3$=H, q=1, x=5, $R_1$=BOC) from 3a (methods A and B).
Rf=0.6 ($CH_2Cl_2$:$CH_3OH$=9:1)
$^1$H-NMR ($CDCl_3$): 7.37–7.15 (m, 5H, Ar); 4.39 (s, 2H, C$\underline{H}_2$ —Ar); 3.63–3.52 (m, 2H, C$\underline{H}_2$OH); 3.25–3.03 (m, 2H, N—$CH_2$); 1.60–1.20 [m, 17H, $CH_2$—(C$\underline{H}_2$)$_4$—$CH_2$ and t.Bu].

6-[N-(N-tert-Butoxycarbonyl-3-trifluoromethylphenyl)methyl-amino]-hexan-1-ol (4b)

($R_3$=3-$CF_3$, q=1, x=5, $R_1$=BOC) from 3b (method A).
Rf=0.61 ($CH_2Cl_2$:$CH_3OH$=9:1)
$^1$H-NMR ($CDCl_3$): 1.26–1.68 (m, 17H, 4$CH_2$ and t.Bu); 3.20 (bs, 2H, $CH_2$N); 3.60 (q, 2H, $J_1$=6.1 Hz, $J_2$=11.3 Hz, $CH_2$O); 4.44 (bs, 2H, $CH_2Ph$); 7.40–7.47 (m, 4H, H arom.).

6-[N-(N-tert-Butoxycarbonyl-2-trifluoromethyl-phenyl)methyl-amino]-hexan-1-ol (4c)

($R_3$=2-$CF_3$, q=1, x=5, $R_1$=BOC) from 3c (method A).
Rf=0.36 ($CH_2Cl_2$:$CH_3OH$=9.5:0.5)

5-(N-tert-Butoxycarbonyl-N-phenylmethylamino)-pentan-1-ol (4d)

($R_3$=H, q=1, x=4, $R_1$=BOC) from 3d (methods A and B).
Rf=0.5 ($CH_2Cl_2$:$CH_3OH$=9:1)
$^1$H-NMR ($CDCl_3$): 7.37–7.15 (m, 5H, Ar); 4.40 (s, 2H, C$\underline{H}_2$ —Ar); 3.64–3.52 (m, 2H, C$\underline{H}_2$OH); 3.27–3.05 (m, 2H, N—$CH_2$); 1.63–1.20 [m, 6H, $CH_2$—(C$\underline{H}_2$)$_3$—$CH_2$]; 1.45 (s, 9H, t.Bu).

4-(N-tert-Butoxycarbonyl-N-phenylmethylamino)-butan-1-ol (4e)

($R_3$=H, q=1, x=3, $R_1$=BOC) from 3e (method B).
$^1$H-NMR ($CDCl_3$): 7.37–7.15 (m, 5H, Ar); 4.40 (s, 2H, C$\underline{H}_2$ —Ar); 3.65–3.55 (m, 2H, C$\underline{H}_2$OH); 3.30–3.10 (m, 2H, N—$CH_2$); 1.63–1.45 [m, 4H, $CH_2$—(C$\underline{H}_2$)$_2$—$CH_2$]; 1.47 (s, 9H, t.Bu).

3-(N-tert-Butoxycarbonyl-N-phenylmethylamino)-propan-1-ol (4f)

($R_3$=H, q=1, x=2, $R_1$=BOC) from 3f (method B).
$^1$H-NMR ($CDCl_3$): 7.37–7.15 (m, 5H, Ar); 4.38 (s, 2H, C$\underline{H}_2$ —Ar); 3.58–3.50 (m, 2H, C$\underline{H}_2$OH); 3.40–3.30 (m, 2H, N—$CH_2$); 3.10 (bs, 1H, OH); 1.70–1.55 (m, 2H, $CH_2$—C$\underline{H}_2$—$CH_2$); 1.40 (s, 9H, t.Bu).

2-(N-tert-Butoxycarbonyl-N-phenylmethylamino)-ethanol (4g)

($R_3$=H, q=1, x=1, $R_1$=BOC) from 2-Phenylmethylamino-ethanol (method A), commercially available.

Rf=0.40 ($CH_2Cl_2$:$CH_3OH$=9.5:0.5)

EXAMPLE 3A

Preparation of the compounds of formual 5 (II—r=0)

A solution containing 1 equivalent of a compound of formula 4, prepared as described in example 2A, a catalytic amount of TEMPO, a catalytic amount of Aliquat®, a catalytic amount of KBr, 1 portion of a saturated $NaHCO_3$ solution and 3 portions of $CH_2Cl_2$ at 0° C. was prepared. A solution of NaClO (pH=8) was added to the solution at 0° C. Aliquots of NaClO solution were added in a 5 hour period up to the disappearance of the starting compound. After 5 hours at room temperature, a 1N NaOH solution was added up to pH 12. The mixture was kept under stirring for 2 hours and then the pH was brought to 4 by addition of a 1N HCl solution. The resulting mixture was extracted with AcOEt (3 times). The organic phases were dried on $Na_2SO_4$ and, after evaporation, an oil which was purified by column or thin layer chromatography was obtained.

The following compounds of formula 5 were obtained:

6-(N-tert-Butoxycarbonyl-N-phenylmethylamino)-hexanoic acid (5a)

($R_3$=H, q=1, x=5, $R_1$=BOC) from 4a.

Rf=0.53 ($CH_2Cl_2$:AcOEt=6:4)

$^1$H-NMR (200 MHz, $CDCl_3$): 7.35–7.15 (m, 5H, Ar); 4.40 (s, 2H, C$\underline{H}_2$—Ar); 3.25–3.05 (m, 2H, $CH_2$—N); 2.30 (t, 2H, C$\underline{H}_2$—COOH); 1.70–1.20 [m, 15H, $CH_2$—(C$\underline{H}_2$)$_3$—$CH_2$ and t.Bu].

6-[N-tert-Butoxycarbonyl-N-(3trifluoromethylphenyl) methyl-amino]-hexanoic acid (5b)

($R_3$=3-$CF_3$, q=1, x=5, $R_1$=BOC) from 4b.

Rf=0.47 ($CH_2Cl_2$:$CH_3OH$=9:1)

$^1$H-NMR ($CDCl_3$): 1.15–1.43 (m, 15H, 3$CH_2$ and t.Bu); 2.17 (bs, 2H, $CH_2CO$); 3.14 (bs, 2H, $CH_2N$); 4.49 (bs, 2H, $CH_2Ph$); 7.36–7.66 (m, 4H, H arom.).

6-[N-tert-Butoxycarbonyl-N-(2-trifluoromethylphenyl) methyl-amino]-hexanoic acid (5c)

($R_3$=2-$CF_3$, q=1, x=5, $R_1$=BOC) from 4c.

Rf=0.40 ($CH_2Cl_2$:$CH_3OH$=9:1)

5-(N-tert-Butoxycarbonyl-N-phenylmethylamino)-pentanoic acid (5d)

($R_3$=H, q=1, x=4, $R_1$=BOC) from 4d.

$^1$H-NMR (200 Mhz, $CDCl_3$): 7.37–7.15 (m, 5H, Ar); 4.40 (s, 2H, C$\underline{H}_2$—Ar); 3.25–3.07 (m, 2H, $CH_2$—N); 2.48–2.25 (m, 2H, C$\underline{H}_2$—COOH); 1.70–1.37 [m, 13H, $CH_2$—C$\underline{H}_2$—$CH_2$ and t.Bu).

4-(N-tert-Butoxycarbonyl-N-phenylmethylamino)-butanoic acid (5e)

($R_3$=H, q=1, x=3, $R_1$=BOC) from 4e.

$^1$H-NMR (200 MHz, $CDCl_3$): 8.90 (bs, COOH); 7.36–7.15 (m, 5H, Ar); 4.41 (s, 2H, C$\underline{H}_2$—Ar); 3.33–3.10 (m, 2H, $CH_2$—N); 2.38–2.25 (m, 2H, C$\underline{H}_2$—COOH); 1.90–1.70 (m, 2H, $CH_2$—C$\underline{H}_2$—$CH_2$]; 1.45 (s, 9H, t.Bu).

N-tert-Butoxycarbonyl-N-phenylmethylaminoacetic acid (5g)

($R_3$=H, q=1, x=1, $R_1$=BOC) from 4g.

Rf=0.40 (hexane:AcOEt=1:1)

$^1$H-NMR ($CDCl_3$): 1.25 (m, 9H, t.Bu), 3.65 (d, 2H, $CH_2N$); 4.30 (d, 2H, $CH_2Ph$); 6.95–7.15 (m, 5H, H arom.); 9.85 (bs, 1H, OH).

EXAMPLE 4A

Preparation of the compounds of formula 6

To 1 equivalent of a compound of formula 4, prepared as described in example 2A, 1.1 equivalents of recrystallized TsCl, dissolved in $Et_2O$ were added. A large excess of $Et_3N$ (30 equivalents) was added to this mixture.

The mixture was kept under stirring overnight at room temperature and for further 2 hours under reflux. After cooling, the mixture was evaporated, the residue was washed with water and extracted with $CH_2Cl_2$. After drying on $Na_2SO_4$ and evaporation, the residue was purified by flash-chromatography.

The following compounds of formula 6 were obtained:

6-(N-tert-Butoxycarbonyl-N-phenylmethylamino)-hexyl-4-toluene sulfonate (6a)

($R_3$=H, q=1, x=5, $R_1$=BOC, A=Ts) from 4a.

Rf=0.5 (AcOEt:hexane=1:1)

6-[N-tert-Butoxycarbonyl-N-(2-trifluoromethylphenyl) methyl-amino]-hexyl-4-toluene sulfonate(6c)

($R_3$=2-$CF_3$, q=1, x=5, $R_1$=BOC, A=Ts) from 4c.

5-(N-tert-Butoxycarbonyl-N-phenylmethylamino)-pentyl-4-toluene sulfonate (6d)

($R_3$=H, q=1, x=4, $R_1$=BOC, A=Ts) from 4d.

Rf=0.12 (AcOEt:hexane=1:9)

EXAMPLE 5A

Preparation of the compounds of formula 7

A catalytic amount of TEMPO and an aqueous solution of KBr were added to 1 equivalent of a compound of formula 4, prepared as described in example 2A, dissolved in $CH_2Cl_2$.

The reaction mixture was cooled at 0° C. and a solution of NaClO at pH 8.7 was slowly added under stirring.

The phases were extracted several times with $CH_2Cl_2$, washing the organic extract with water.

The organic phases were dried on $Na_2SO_4$.

After filtration the solvent was evaporated under reduced pressure.

The following compounds of formula 7 were obtained:

5-(N-tert-Butoxycarbonyl-N-phenylmethylamino)-pentanal (7d)

($R_3$=H, q=1, x=4, $R_1$=BOC) from 4d.

$^1$H-NMR ($CDCl_3$): 9.70 (bs, 1H, CHO); 7.37–7.15 (m, 5H, Ar); 4.40 (s, 2H, C$\underline{H}_2$—Ar); 3.25–3.05 (m, 2H, N—$CH_2$); 2.45–2.33 (m, 2H, $CH_2$—COO); 1.61–1.36 [m, 13H, $CH_2$—(C$\underline{H}_2$)$_2$—$CH_2$ and t.Bu).

4-(N-tert-Butoxycarbonyl-N-phenylmethylamino)-butanal (7e)

($R_3$=H, q=1, x3, $R_1$=BOC) from 4e.

$^1$H-NMR ($CDCl_3$): 9.21 (t, 1H, CHO); 7.37–7.15 (m, 5H, Ar); 4.40 (s, 2H, C$\underline{H}_2$—Ar); 3.28–3.10 (m, 2H, N—$CH_2$); 2.47–2.32 (m, 2H, C$\underline{H}_2$—CHO); 1.90–1.73 (m, 2H, $CH_2$—C$\underline{H}_2$—$CH_2$]; 1.47 (s, 9H, t.Bu).

3-(N-tert-Butoxycarbonyl-N-phenylmethylamino)-propanal (7f)

($R_3$=H, q=1, x=2, $R_1$=BOC) from 4f.

$^1$H-NMR ($CDCl_3$): 9.70 (s, 1H, CHO); 7.35–7.15 (m, 5H, H arom.); 4.41 (s, 2H, C$\underline{H}_2$—Ar); 3.55–3.40 (m, 2H, C$\underline{H}_2$—OH); 2.70–2.50 (m, 2H, C$\underline{H}_2$—CHO); 1.45 (m, 9H, t.Bu).

EXAMPLE 6A

Preparation of the compounds of formula 8

Method A

To 1 equivalent of a compound of formula 6, prepared as described in example 4A, dissolved in anhydrous DMF 1.1 equivalents of an aminoalcohol 1' and 5 equivalents of $K_2CO_3$ were added. The solution was heated at 100° C. for 6 hours. After filtration, DMF was evaporated under vacuum and the residue was washed with water and extracted with AcOEt. After drying on $Na_2SO_4$ and evaporation, the residue was purified by flash-chromatography.

Method B

To 1 equivalent of an aminoalcohol 1' in ethanol, in the presence of 3 Å molecular sieves, 1 equivalent of an aldehyde 7, prepared as described in example 5A, was added and the mixture was kept under stirring for 2.5 hours. After filtration of the molecular sieves, $NABH_4$ was added portionwise to the resultant solution under stirring, under nitrogen atmosphere and by keeping the temperature at 15–20° C. After 1.5 hours, the solvent was evaporated under reduced pressure and the residue was taken with water.

After extraction with $Et_2O$, the organic phases were washed with a NaCl solution and dried on $Na_2SO_4$.

The solvent was evaporated under reduced pressure.

The following compounds of formula 8 were obtained:

6-[6-(N-tert-Butoxycarbonyl-N-phenylmethylamino)-hexylamino]-hexan-1-ol (8a)

($R_3$=H, q=1, y=6, m=5, $R_1$=BOC) from 6a and 1'a.

Rf=0.35 ($CH_3OH$)

6-[6-[N-tert-Butoxycarbonyl-N-(2-trifluoromethylphenyl)methylamino]-hexylamino]-hexan-1-ol (8b)

($R_3$=2-$CF_3$, q=1, y=6, m=5, $R_1$=BOC) from 6c and 1a.

6-[5-(N-tert-Butoxycarbonyl-N-phenylmethylamino)-pentylamino]-hexan-1ol (8c)

($R_3$=H, q=1, y=5, m=5, $R_1$=BOC) from 6d and 1'a and from 7d and 1'a.

Rf=0.21 (AcOEt:$CH_3OH$=1:1)

$^1$H-NMR ($CDCl_3$): 7.35–7.15 (m, 5H,Ar); 4.39 (s, 2H, C$\underline{H}_2$ —Ar); 3.61 (t, 2H, C$\underline{H}_2$—OH); 3.25–3.05 (m, 2H, N—$CH_2$); 2.60–2.48 (m, 4H, C$\underline{H}_2$—NH—C$\underline{H}_2$); 1.60–1.20 [m, 23H, $CH_2$—(C$\underline{H}_2$)$_3$—$CH_2$, N—$CH_2$—(C$\underline{H}_2$)$_4$—$CH_2$ and t.Bu].

5-[5-(N-tert-Butoxycarbonyl-N-phenylmethylamino)-pentylamino]-pentan-1-ol (8d)

($R_3$=H, q=1, y=5, m=4, $R_1$=BOC) from 6d and 1'b and from 7d and 1'b.

Rf=0.23 (AcOEt: $CH_3OH$=1:1)

$^1$H-NMR ($CDCl_3$): 7.33–7.13 (m, 5H,Ar); 4.39 (s 2H, C$\underline{H}_2$—Ar); 3.65–3.55 (m, 2H, $CH_2$—O); 3.23–3.05 (m, 2H, Ar—$CH_2$—N—C$\underline{H}_2$); 2.61–2.50 (m, 4H, C$\underline{H}_2$—NH—C$\underline{H}_2$); 1.65–1.20 [m, 21H, $CH_2$—(C$\underline{H}_2$)$_3$—$CH_2$, N—$CH_2$—(C$\underline{H}_2$)$_3$—$CH_2$ and t.Bu].

5-[6-(N-tert-Butoxycarbonyl-N-phenylmethylamino)-hexylamino]-pentan-1-ol (8e)

($R_3$=H, q=1, y=6, m=4, $R_1$=BOC) from 6a and 1'b.

6-[3-(N-tert-Butoxycarbonyl-N-phenylmethylamino)-propylamino]-hexan-1-ol (8f)

($R_3$=H, q=1, y=3, m=5, $R_1$=BOC) from 7f and 1'a.

$^1$H-NMR ($CDCl_3$): 7.33–7.13 (m, 5H,Ar); 4.40 (s, 2H, C$\underline{H}_2$—Ar); 3.58 (t, 2H, C$\underline{H}_2$—OH); 3.30–3.10 (m, 2H, Ar—$CH_2$—N—C$\underline{H}_2$); 2.51 (t, 4H, C$\underline{H}_2$—NH—C$\underline{H}_2$); 1.70–1.20 [m, 19H, $CH_2$—(C$\underline{H}_2$)$_4$—$CH_2$, N—$CH_2$—C$\underline{H}_2$—$CH_2$ and t.Bu].

6-[4-(N-tert-Butoxycarbonyl-N-phenylmethylamino)-butylamino]-hexan-1-ol (8g)

($R_3$=H, q=1, y=4, m=5, $R_1$=BOC) from 7e and 1'a.

$^1$H-NMR ($CDCl_3$): 7.35–7.15 (m, 5H, Ar); 4.39 (s, 2H, C$\underline{H}_2$—Ar); 3.59 (t, 2H, C$\underline{H}_2$—OH); 3.25–3.00 (m, 2H, N—$CH_2$); 2.58–2.50 (m, 4H, C$\underline{H}_2$—NH—C$\underline{H}_2$); 1.60–1.20 [m, 21H, $CH_2$—(C$\underline{H}_2$)$_2$—$CH_2$, N—$CH_2$—(C$\underline{H}_2$)$_4$—$CH_2$ and t.Bu].

5-[3-(N-tert-Butoxycarbonyl-N-phenylmethylamino)-propylamino]-pentan-1-ol (8h)

($R_3$=H, q=1, y=3, m=4, $R_1$=BOC) from 7 f and 1'b.

$^1$H-NMR ($CDCl_3$): 7.33–7.10 (m, 5H, Ar); 4.40 (s, 2H, C$\underline{H}_2$—Ar); 3.59 (t, 2H, C$\underline{H}_2$—OH); 3.30–3.10 (m, 2H, Ar—$CH_2$—N—C$\underline{H}_2$) 2.58–2.48 (m, 4H, C$\underline{H}_2$—NH—C$\underline{H}_2$); 1.70–1.20 [m, 17H, $CH_2$—(C$\underline{H}_2$)$_3$—$CH_2$, N—$CH_2$—C$\underline{H}_2$—$CH_2$ and t.Bu].

3-[5-(N-tert-Butoxycarbonyl-N-phenylmethylamino)-pentylamino]-propan-1-ol (8i)

($R_3$=H, q=1, y=5, m=2, $R_1$=BOC) from 7d and 1'd.

$^1$H-NMR ($CDCl_3$): 7.33–7.13 (m, 5H, Ar); 4.40 (s, 2H, C$\underline{H}_2$—Ar); 3.80–3.73 (m, 2H, $CH_2$—O); 3.23–3.05 (m, 2H, Ar—$CH_2$—N—C$\underline{H}_2$); 2.88–2.80 (m, 2H, N—C$\underline{H}_2$—$CH_2$—OH); 2.60–2.50 [m, 2H, ($CH_2$)$_4$—C$\underline{H}_2$—N]; 1.70–1.30 [m, 17H, $CH_2$—(C$\underline{H}_2$)$_3$—$CH_2$, $CH_2$—C$\underline{H}_2$—$CH_2$ and t.Bu].

EXAMPLE 7A

Preparation of the compounds of formula 9

Method A

To 1 equivalent of a compound of formula 8, prepared as described in example 6A, dissolved in anhydrous $CH_2Cl_2$ 1.1 equivalents of $BOC_2O$ dissolved in $CH_2Cl_2$ at 0° C. were added dropwise. After keeping under stirring for 3 hours at room temperature, the solvent was evaporated, the residue was washed with water and extracted with $CH_2Cl_2$. After drying and evaporation, an oily residue which was used without further purification was obtained.

Method B $BOC_2O$ dissolved in a little dioxane was added dropwise to 1 equivalent of a compound of formula 8, prepared as described in example 6A, dissolved in a 2:1 dioxane:water mixture under stirring at 0° C.

The reaction mixture was brought to room temperature and after 2.5 hours the solution was concentrated by evaporating dioxane under reduced pressure.

After extraction with AcOEt, drying on $Na_2SO_4$ and filtration, the solvent was evaporated under reduced pressure.

The crude was purified by flash chromatography on silica.

Method C

To 1 equivalent of a compound of formula 8 ($R_1$=H), prepared as described in the patent application WO 96/18633, dissolved in $CH_2Cl_2$ 2.2 equivalents of $BOC_2O$ dissolved in $CH_2Cl_2$ at 0° C. were added dropwise. The mixture was kept under stirring for 3 hours at 0° C. and for further 4 hours at room temperature. After evaporation of the solvent, the residue was isolated and used without further purification.

The following compounds of formula 9 were obtained:

6-[6-(N'-tert-Butoxycarbonyl-N'-phenylmethylamino)-N-tert-butoxycarbonyl-hexylamino]-hexan-1-ol (9a)

($R_3$=H, q=1, y=6, m=5, $R_1$=$R_2$=BOC) from 8a (method A).

Rf=0.54 (AcOEt:hexane=1:1)

6-[6-[N'-tert-Butoxycarbonyl-N'-(2-trifluoromethylphenyl)methylamino]-N-tert-butoxycarbonyl-hexylamino]-hexan-1-ol (9b)

($R_3$=2-$CF_3$, q=1, y=6, m=5, $R_1$=$R_2$=BOC) from 8b (method A).

6-[5-(N'-tert-Butoxycarbonyl-N'-phenylmethylamino)-N-tert-butoxycarbonyl-pentylamino]-hexan-1-ol (9c)

($R_3$=H, q=1, y=5, m=5, $R_1$=$R_2$=BOC) from 8c (methods A and B).

Rf=0.40 (AcOEt:hexane=1:1)

$^1$H-NMR ($CDCl_3$): 1.16–1.58 (m, 32H, 7$CH_2$ and 2t.Bu); 3.10 (bs, 6H, 3$CH_2$N); 3.61 (t, 2H, J=6.2 Hz, $CH_2$O); 4.40 (bs, 2H, $CH_2$Ph); 7.22–7.30 (m, 5H, H arom.).

5-[5-(N'-tert-Butoxycarbonyl-N'-phenylmethylamino)-N-tert-butoxycarbonyl-pentylamino]-pentan-1-ol (9d)

($R_3$=H, q=1, y=5, m=4, $R_1$=$R_2$=BOC) from 8d (methods A and B).

Rf=0.5 (AcOEt:hexane=1:1)

$^1$H-NMR (CDCl$_3$): 7.35–7.15 (m, 5H, Ar); 4.40 (s, 2H, CH$_2$—Ar); 3.65–3.55 (m, 2H, CH$_2$—O); 3.20–3.03 (m, 6H, Ar—CH$_2$—N—CH$_2$ and CH$_2$—N—CH$_2$); 1.65–1.10 [m, 30H, CH$_2$—(CH$_2$)$_3$—CH$_2$, N—CH$_2$—(CH$_2$)$_3$—CH$_2$ and t.Bu].

5-[6-(N'-tert-Butoxycarbonyl-N'-phenylmethylamino)-N-tert-butoxycarbonyl-hexylamino]-pentan-1-ol (9e)

(R$_3$=H, q=1, y=6, m=4, R$_1$=R$_2$=BOC) from 8e (method A).

Rf=0.45 (AcOEt:hexane=1:1)

6-[3(N'-tert-Butoxycarbonyl-N'-phenylmethylamino)-N-tert-butoxycarbonyl-propylamino]-hexan-1-ol (9f)

(R$_3$=H, q=1, y=3, m=5, R$_1$=R$_2$=BOC) from 8f (method A).

$^1$H-NMR (CDCl$_3$): 7.35–7.13 (m, 5H, Ar); 4.40 (s, 2H, CH$_2$—Ar); 3.60 (t, 2H, CH$_2$—OH); 3.25–3.00 (m, 6H, CH$_2$—NCOO); 1.80–1.20 [m, 28H, CH$_2$—(CH$_2$)$_4$—CH$_2$, CH$_2$—CH$_2$—CH$_2$ and t.Bu].

6-[4-(N'-tert-Butoxycarbonyl-N'-phenylmethylamino)-N-tert-butoxycarbonyl-butylamino]-hexan-1-ol (9g)

(R$_3$=H, q=1, y=4, m=5, R$_1$=R$_2$=BOC) from 8g (method B).

$^1$H-NMR (CDCl$_3$): 7.33–7.15 (m, 5H, Ar); 4.39 (s, 2H, CH$_2$—Ar); 3.67–3.53 (m, 2H, CH$_2$ —OH); 3.25–3.00 (m, 6H, Ar—N—CH$_2$ and CH$_2$—N—CH$_2$); 1.60–1.15 [m, 30H, CH$_2$—(CH$_2$)$_2$—CH$_2$, N—CH$_2$—(CH$_2$)$_4$—CH$_2$ and t.Bu].

5-[3-(N'-tert-Butoxycarbonyl-N'-phenylmethylamino)-N-tert-butoxycarbonyl-propylamino]-pentan-1-ol (9h)

(R$_3$=H, q=1, y=3, m=4, R$_1$=R$_2$=BOC) from 8h (methods A and B).

$^1$H-NMR (CDCl$_3$): 7.35–7.13 (m, 5H, Ar); 4.40 (s, 2H, CH$_2$—Ar); 3.61 (t, 2H, CH$_2$—OH); 3.25–3.00 (m, 6H, CH$_2$—NCOO); 1.80–1.20 [m, 26H, CH$_2$—(CH$_2$)$_3$—CH$_2$, CH$_2$—CH$_2$—CH$_2$ and t.Bu].

3-[5-(N'-tert-Butoxycarbonyl-N'-phenylmethylamino)-N-tert-butoxycarbonyl-pentylamino]-propan-1-ol (9i)

(R$_3$=H, q=1, y=5, m=2, R$_1$=R$_2$=BOC) from 8i (method B).

$^1$H-NMR (CDCl$_3$): 7.33–7.15 (m, 5H, Ar); 4.39 (s, 2H, CH$_2$—Ar); 3.60–3.49 (m, 2H, CH$_2$—O); 3.35–3.00 (m, 6H, Ar—CH$_2$—N—CH$_2$ and CH$_2$—N—CH$_2$); 2.90 (bs, 1H, OH); 1.60–1.10 [m, 30H, CH$_2$—(CH$_2$)$_3$—CH$_2$, N—CH$_2$—CH$_2$—CH$_2$ and t.Bu].

2-[6-(N'-tert-Butoxycarbonyl-N'-phenylmethylamino)-N-tert-butoxycarbonyl-hexylamino]-ethanol (9k)

(R$_3$=H, q=1, y=6, m=1, R$_1$=R$_2$=BOC) from 2-[6-(Phenylmethylamino)-hexylamino]-ethanol (method C).

2-[6-[N'-tert-Butoxycarbonyl-N'-(4-methoxyphenyl)methylamino]-N-tert-butoxycarbonyl-hexylamino]-ethanol (9l)

(R$_3$=4-OCH$_3$, q=1, y=6, m=1, R$_1$=R$_2$=BOC) from 2-[6-[(4-Methoxyphenyl)methyl-amino]-hexylamino]-ethanol (method C).

Rf=0.36 (AcOEt)

5-[4-(N'-tert-Butoxycarbonyl-N'-phenylmethylamino)-N-tert-butoxycarbonyl-butylamino]-pentan-1-ol (9m)

(R$_3$=H, q=1, y=4, m=4, R$_1$=R$_2$=BOC) from 5-[4-(Phenylmethylamino)-butylamino]-pentan-1-ol (method C).

Rf=0.36 (AcOEt:hexane=1:1)

EXAMPLE 8A

Preparation of the compounds of formula 10 (II—r=1)

Method A

To 1 equivalent of a compound of formula 9, prepared as described in example 7A, dissolved in DMF 3.5 equivalents of pyridinium dichromate were added in 3 portions at room temperature. The dark mixture was kept under stirring overnight. The reaction mixture was then evaporated under vacuum, AcOEt was added to the residue and the resultant solution was filtered. After drying on Na$_2$SO$_4$ and evaporation, the resultant residue was purified by column or thin layer chromatography.

Method B

At 0° C. a solution containing 1 equivalent of a compound of formula 9, prepared as described in example 7A, a catalytic amount of TEMPO, a catalytic amount of Aliquate®, a catalytic amount of KBr, 1 portion of a saturated NAHCO$_3$ solution and 3 portions of CH$_2$Cl$_2$ was prepared. A solution of NaClO (pH=8) was added to the solution at 0° C. Aliquots of NaClO solution were added in 5 hours period up to the disappearance of the starting compound. After 5 hours at room temperature, a 1N NaOH solution was added up to pH 12. The mixture was kept under stirring for 2 hours and then the pH was brought to 4 by addition of a 1N HCl solution. The resultant mixture was extracted with AcOEt (3 times). The organic phases were dried on Na$_2$SO$_4$ and, after evaporation, an oil which was purified by column or thin layer chromatography was obtained.

The following compounds of formula 10 were obtained:

6-[6-(N'-tert-Butoxycarbonyl-N'-phenylmethylamino)-N-tert-butoxycarbonyl-hexylamino]-hexanoic acid (10a)

(R$_3$=H, q=1, y=6, m=5, R$_1$=R$_2$=BOC) from 9a (methods A and B).

Rf=0.33 (AcOEt:hexane=1:1)

$^1$H-NMR (CDCl$_3$): 7.33–7.15 (m, 5H, Ar); 4.40 (s, 2H, CH$_2$—Ar); 3.25–3.00 (m, 6H, Ar—N—CH$_2$ and CH$_2$—N—CH$_2$); 2.39–2.28 (m, 2H, CH$_2$—COO); 1.70–1.10 [m, 30H, CH$_2$—(CH$_2$)$_3$—CH$_2$, N—CH$_2$—(CH$_2$)$_3$—CH$_2$ and t.Bu].

6-[6-[N'-tert-Butoxycarbonyl-N'-(2-trifluoromethylphenyl)methylamino]-N-tert-butoxycarbonyl-hexylamino]-hexanoic acid (10b)

(R$_3$=2-CF$_3$, q=1, y=6, m=5, R$_1$=R$_2$=BOC) from 9b (method A).

6-[5-(N'-tert-Butoxycarbonyl-N'-phenylmethylamino)-N-tert-butoxycarbonyl-pentylamino]-hexanoic acid (10c)

(R$_3$=H, q=1, y=5, m=5, R$_1$=R$_2$=BOC) from 9c (methods A and B).

Rf=0.4 (AcOEt:hexane=1:1)

$^1$H-NMR (CDCl$_3$): 1.14–1.68 (m, 30H, 6CH$_2$ and 2t.Bu); 2.20 (bs, 2H, CH$_1$C); 3.05 (Bs, 6H, 3CH$_2$N); 4.35 (bs, 2H, CH$_2$Ph); 7.17–7.29 (m, 5H, H arom.).

5-[5-N'-tert-Butoxycarbonyl-N'-phenylmethylamino)-N-tert-butoxycarbonyl-pentylamino]-pentanoic acid (10d)

(R$_3$=H, q=1, y=5, m=4, R$_1$=R$_2$=BOC) from 9d (method B).

Rf=0.36 (AcOEt:hexane=1:1)

$^1$H-NMR (200 Mhz, CDCl$_3$): 7.33–7.15 (m, 5H, Ar); 4.39 (s, 2H, CH$_2$—Ar); 3.20–3.03 (m, 6H, Ar—CH$_2$—N—CH$_2$ and CH$_2$—N—CH$_2$); 2.38–2.30 (m, 2H, CH$_2$—COO); 1.60–1.10 (m, 28H, CH$_2$—(CH$_2$)$_3$—CH$_2$, N—CH$_2$—(CH$_2$)$_3$—CH$_2$ and t.Bu).

5-[6-(N'-tert-Butoxycarbonyl-N'-phenylmethylamino)-N-tert-butoxycarbonyl-hexylamino]-pentanoic acid (10e)

(R$_3$=H, q=1, y=6, m=4, R$_1$=R$_2$=BOC) from 9e (method A).

Rf=0.18 (AcOEt:hexane=1:1)

6-[3(N'-tert-Butoxycarbonyl-N'-phenylmethylamino)-N-tert-butoxycarbonyl-propylamino]-hexanoic acid (10f)

(R$_3$=H, q=1, y=3, m=5, R$_1$=R$_2$=BOC) from 9f (method B).

$^1$H-NMR (200 MHz, CDCl$_3$): 7.35–7.13 (m, 5H, Ar); 6.10 (bs, 1H, COOH); 4.40 (s, 2H, CH$_2$—Ar); 3.25–3.00 (m, 6H, 3CH$_2$—NCOO); 2.31 (t, 2H, CH$_2$—COO): 1.80–1.20 (m, 26H, CH$_2$—(CH$_2$)$_3$—CH$_2$, CH$_2$—CH$_2$—CH$_2$ and t.Bu).

6-[4-(N'-tert-Butoxycarbonyl-N'-phenylmethylamino)-N-tert-butoxycarbonyl-butylamino]-hexanoic acid (10g)

($R_3$=H, q=1, y=4, m=5, $R_1$=$R_2$=BOC) from 9g (method B).

$^1$H-NMR (200 MHz, CDCl$_3$): 7.33–7.15 (m, 5H, Ar); 4.39 (s, 2H, C$\underline{H}_2$—Ar); 3.25–3.00 (m, 6H, Ar—N—C$\underline{H}_2$ and C$\underline{H}_2$—N—C$\underline{H}_2$); 2.31 (t, 2H, C$\underline{H}_2$—COO); 1.70–1.10 (m, 28H, CH$_2$—(CH$_2$)$_2$—CH$_2$, N—CH$_2$—(C$\underline{H}_2$)$_3$—CH$_2$ and t.Bu).

5-[3N'-tert-Butoxycarbonyl-N'-phenylmethylamino)-N-tert-butoxycarbonyl-propylamino]-pentanoic acid (10h)

($R_3$=H, q=1, y=3, m=4, $R_1$=$R_2$=BOC) from 9h (method B).

$^1$H-NMR (200 Mz, CDCl$_3$): 7.60 (bs, 1H, COOH); 7.35–7.13 (m, 5H, Ar); 4.40 (s, 2H, C$\underline{H}_2$—Ar); 3.205–2,983.00 (m, 6H, 3$\underline{H}_2$—NCOO); 2.25–2.15 (m, 2H, C$\underline{H}_2$—COO); 1.80–1.20 (m, 24H, CH$_2$—(CH$_2$)$_2$—CH$_2$, CH$_2$—C$\underline{H}_2$—CH$_2$ and t.Bu).

3-[5-(N'-tert-Butoxycarbonyl-N'-phenylmethylamino)-N-tert-butoxycarbonyl-pentylamino]-propanoic acid (10i)

($R_3$=H, q=1, y=5, m=2, $R_1$=$R_2$=BOC) from 9i (method B).

$^1$H-NMR (200 MHz, CDCl$_3$): 7.33–7.15 (m, 5H, Ar); 4.39 (s, 2H, C$\underline{H}_2$—Ar); 3.48–3.05 (m, 6H, Ar—CH$_2$—N—C$\underline{H}_2$ and C$\underline{H}_2$—N—C$\underline{H}_2$); 2.60–2.50 (m, 2H, C$\underline{H}_2$—COO); 1.60–1.20 (m, 24H, CH$_2$—(C$\underline{H}_2$)$_3$—CH$_2$ and t.Bu).

[6-(N'-tert-Butoxycarbonyl-N'-phenylmethylamino)-N-tert-butoxycarbonyl-hexylamino]-acetic acid (10k)

($R_3$=H, q=1, y=6, m=1, $R_1$=$R_2$=BOC) from 9k (method A).

Rf=0.22 (AcOEt)

[6-[N'-tert-Butoxycarbonyl-N'-(4-methoxyphenyl) methylamino]-N-tert-butoxycarbonyl-hexylamino]-acetic acid (10)

($R_3$=4-OCH$_3$, q=1, y=6, m=1, $R_1$=$R_2$=BOC) from 9l (method A).

Rf=0.29 (AcOEt:hexane=1:1)

5-[4-(N'-tert-Butoxycarbonyl-N'-phenylmethylamino)-N-tert-butoxycarbonyl-butylamino]-pentanoic acid (10m)

($R_3$=H, q=1, y=4, m=4, $R_1$=$R_2$=BOC) from 9m (method A)

Rf=0.29 (AcOEt)

[6-(N'-Phenylmethoxycarbonyl-N'-phenylmethylamino)-N-phenylmethoxycarbonyl-hexylamino]-acetic acid (10n)

($R_3$=H, q=1, y=6, m=1, $R_1$=$R_2$=BzOCO) from 2-[6-(N'-Phenylmethoxycarbonyl-N'-phenylmethylamino)-N-phenylmethoxycarbonyl-hexylamino]-ethanol, described in WO 96/18633.

Rf=0.24 (AcOEt:CH$_3$OH=95:5) (method A)

EXAMPLE 9A

Preparation of the compounds of formula 5" (II—r=0)

An excess (15 equivalents) of CF$_3$COOH was added to 1 equivalent of a compound of formula 5, prepared as described in example 3A, dissolved in CH$_2$Cl$_2$ at room temperature. After 6 hours under stirring, the solvent was evaporated under vacuum and the resultant residue (compound 5- $R_1$=H) was isolated and used without further purification.

To 1 equivalent of compound 5 ($R_1$=H) in CH$_2$Cl$_2$ 1.1 equivalents of ethylchloroformate and 5 equivalents of diisopropylethylamine were added at 0° C. The reaction mixture was kept under stirring at room temperature overnight. After washing with water and with a saturated NaHCO$_3$ solution, the organic phase was dried on Na$_2$SO$_4$ and evaporated. The resultant oily residue was purified by column or thin layer chromatography.

The following compound of formula 5" was obtained:
6-(N-Ethoxycarbonyl-N-phenylmethylamino)-hexanoic acid (5"a)

($R_3$=H, q=1, x=5, $R_{1a}$=EtOCO) from 5a.
Rf=0.16 (CH$_2$Cl$_2$:CH$_3$OH=9.5:0.5)

EXAMPLE 10A

Preparation of the compounds of formula 10" (II—r=1)

Ethereal hydrochloric acid was added under stirring to 1 equivalent of a compound of formula 10, prepared as described in example 8A, dissolved in a little Et$_2$O. After 5 hours the precipitate was filtered and washed with Et$_2$O obtaining the corresponding compound of formula 10 ($R_1$=$R_2$=H).

An excess of acyl chloride and NaOH were contemporaneously added dropwise to 1 equivalent of the compound of formula 10 ($R_1$=$R_2$=H) in CH$_2$Cl$_2$ and NaOH 1N under stirring at 0° C.

The organic phases were separated and the aqueous phase was extracted with CH$_2$Cl$_2$.

The organic phase was dried on Na$_2$SO$_4$ and evaporated.
The following compounds of formula 10" were obtained:
6-[5-(N'-Acetyl-N'-phenylmethylamino)-N-acetyl-pentylamino]-hexanoic acid (10"a)

($R_3$=H, q=1, y=5, m=5, $R_{1a}$=$R_{2a}$=CH$_3$CO) from 10c.
$^1$H-NMR (200 MHz, CDCl$_3$): 7.40–7.10 (m, 5H, Ar), 4.59–4.50 (s, 2H, C$\underline{H}_2$—Ar): 3.38–3.09 (m, 6H, 3CH$_2$—NCO); 2.38–2.27 (m, 2H, CH$_2$—COO); 2.17–2.03 (5s, 6H, 2COCH$_3$); 1.72–1.12 [m, 12H, 2CH$_2$—(C$\underline{H}_2$)$_3$—CH$_2$).

6-[5-[N'-(2,2-Dimethylpropionyl)-N'-phenylmethylamino]-N-(2,2dimethylpropionyl)-pentylamino]-hexanoic acid (10"b)

[$R_3$=H, q=1, y=5, m=5, $R_{1a}$=$R_{2a}$=(CH$_3$)$_3$CCO] from 10c.
$^1$H-NMR (200 MHz, CDCl$_3$): 7.36–7.12 (m, 5H, Ar), 4.67 (s, 2H, C$\underline{H}_2$—Ar); 3.30–3.15 (m, 6H, 3CH$_2$—NCOO); 2.33 (t, 2H, CH$_2$—COO); 1.70–1.10 [m, 30H, 2CH$_2$—(C$\underline{H}_2$)$_3$—CH$_2$ and t.Bu].

Part B—Synthesis of the Compounds of Formula (I)

EXAMPLE 1B

Preparation of the compounds of formula (I) wherein $R_1$ and $R_2$ are different from hydrogen Method A To 1 equivalent of a compound of formula II, prepared as described in part A, dissolved in CH$_2$Cl$_2$ or in anhydrous DMF (1–5 ml), 1 equivalent of (±)-4-amino-1-(2-hydroxymethyl-1,3-oxathiolan-5-yl)-2(1H)-pyrimidinone followed by a solution of BOP (1.5 equivalents) and Et$_3$N (3 equivalents) was added. The reaction mixture was kept under stirring at room temperature for 3–5 hours. After evaporation to dryness, brine and AcOEt were added. After extraction, the organic phase was dried on Na$_2$SO$_4$ and evaporated obtaining a mixture of compounds of formula I-A, I-B and I-C which were separated by chromatography.

Method B

Under nitrogen atmosphere, 1 equivalent of CDI was added to 1 equivalent of a compound of formula II, prepared as described in part A, dissolved in CHCl$_3$.

After 30 minutes 1 equivalent of (2S,5R)-4-(dimethylamino-methyleneamino)-1-(2-hydroxymethyl-1,3-oxathiolan-5-yl)-2(1H)-pyrimidinone or of the corresponding racemate was added under nitrogen atmosphere and the reaction mixture was heated under-reflux.

After 24 hours the solvent was evaporated under reduced pressure and the residue was taken with AcOEt.

After washing with water and separation of the phases, the organic phase was evaporated under reduced pressure.

The residue was dissolved in a mixture $CH_2Cl_2:CH_3OH=2:1$ and aqueous acetic acid was added.

After one night, the solvent was evaporated under reduced pressure, the residue was washed with a solution of $NaHCO_3$ and the resultant crude was purified by flash-chromatography on silica (eluant $CH_2Cl_2:CH_3OH=95:5$).

The following compounds of formula (I) were obtained:

Compounds of formula I-A (±)-4-Amino-1-[2-[6-[5-(N'-tert-butoxycarbonyl-N'-phenylmethylamino)-N-tert-butoxycarbonyl-pentylamino]-hexanoyloxymethyl]-1,3-oxathiolan-5-yl]-2(1H)-pyrimidinone (Compound 1)

($R_3$=H, q=1, n=5, r=1, m=5, $R_1$=$R_2$=BOC) from $\underline{10}$c (methods A and B).

Rf=0.4 ($CH_2Cl_2:CH_3OH$=9:1)

$^1$H-NMR ($CDCl_3$): 1.72–1.55 (m, 32H, 7$CH_2$ and 2t.Bu); 2.35 (t, 2H, J=7.3 Hz, $CH_2CO$); 3.02–3.10 (m, 6H, $CH_2N$); 3.46–3.55 (m, 2H, 2H-2'); 4.32–4.56 (m, 4H, 2H-5' and $CH_2Ph$); 5.31 (pseudo q, 1H, H-4'); 5.83 (bs, 1H, H-5); 6.33 (pseudo t, 1H, H-1'); 7.17–7.34 (m, 5H, H arom.); 7.67 (d, 1H, J=5.8 Hz, H-6).

Mass (ionization TSP/DI$^+$): 718 [M+H]$^+$, 618 [718-BOC]$^+$, 518 [618-BOC]$^+$ (2S, 5R)-4-Amino-1-[2-[6-[5-(N'-tert-butoxycarbonyl-N'-phenylmethylamino)-N-tert-butoxycarbonyl-pentylamino]-hexanoyloxymethyl]-1,3-oxathiolan-5-yl]-2(1H)-pyrimidinone (Compound 2)

($R_3$=H, q=1, n=5, r=1, m=5, $R_1$=$R_2$=BOC) from $\underline{10}$c (method B).

$^1$H-NMR ($CDCl_3$): 1.08–1.72 [m, 30H, 2$CH_2$—(C$\underline{H}_2$)$_3$—$CH_2$ and 2t.Bu]; 2.35 (t, 2H, $J_{HH}$=7.30 Hz, $CH_2$—CO); 3.04–3.57 (m, 8H, $CH_2$—S and 3$CH_2$—N); 4.32–4.58 (m, 4H, $CH_2$—Ph and COO—$CH_2$); 5.30–5.34 (m, 1H, CH—S); 5.68–5.87 (bs, 1H, C$\underline{H}$=CHN); 6.03–6.43 (bs, 2H, $NH_2$); 6.30–6.35 (m, 1H, N—CH—O); 7.16–7.33 (m, 5H, Ar); 7.73 (d, 1H, $J_{HH}$=7.4 Hz, =CH—N—CO).

Mass (ionization TSP/DI$^+$): 718 [M+H]$^+$ (±)-4-Amino-1-[2-[6-[6-(N'-tert-butoxycarbonyl-N'-phenylmethylamino)-N-tert-butoxycarbonyl-hexylamino]-hexanoyloxymethyl]-1,3-oxathiolan-5-yl]-2(1H)-pyrimidinone (Compound 3)

($R_3$=H, q=1, n=6, r=1, m=5, $R_1$=$R_2$=BOC) from $\underline{10}$a (method A).

Rf=0.14 (AcOEt)

$^1$H-NMR ($CDCl_3$): 1.15–1.67 (m, 32H, 7$CH_2$ and 2t.Bu); 2.35–2.42 (m, 2H,$CH_2CO$); 2.93–3.17 (m, 7H, 3$CH_2N$ and H-2'a or H-2'b); 3.50–3.59 (m, 1H, H-2'a or H-2'b); 3.83–4.10 (m, 2H, 2H-5'); 4.34 (bs, 2H, $CH_2Ph$); 5.26 (pseudo d, 1H, H-4'); 6.26 (pseudo d, 1H, H-1'); 7.12–7.29 (m, 5H, H arom.); 7.35 (d, 1H, J=7.5 Hz, H-5); 8.37 (d, 1H, J=7.5 Hz, H-6).

(±)-4-Amino-1-[2-[6-(N-tert-butoxycarbonyl-N-phenylmethylamino)-hexanoyloxy-methyl]-1,3-oxathiolan-5-yl]-2(1H)-pyrimidinone (Compound 4)

($R_3$=H, q=1, n=5, r=0, $R_1$=BOC) from $\underline{5}$a (methods A and B).

Rf=0.42 (AcOEt)

$^1$H-NMR ($CDCl_3$): 1.10–1.66 (m, 15H, 3$CH_2$ and t.Bu); 2.26 (t, 2H, J=7.5 Hz, $CH_2CO$); 2.96–3.07 (m, 3H, $CH_2N$ and H-2'a or H-2'b); 3.42–3.51 (m, 1H, H-2'a or H-2'b); 4.26–4.32 (m, 3H, $CH_2Ph$ and H-5'a or H-5'b); 4.43–4.52 (m, 1H, H-5'a or H-5'b); 5.25 (q, 1H, $J_1$=3.2 Hz, $J_2$=5.0 Hz, H-4'); 5.72 (bs, 1H, H-5); 6.25 (pseudo t, 1H, H-1'); 7.10–7.40 (m, 5H, H arom.); 7.67 (d, 1H, J=7.3 Hz, H-6).

Mass (ionization TSP/DI$^+$): 533 [M+H]$^+$, 555 [M+Na]$^+$, 252 [230+Na]$^+$, 459

(2S,5R)-4-Amino-1-[2-[6-(N-tert-butoxycarbonyl-N-phenylmethylamino)-hexanoyloxymethyl]-1,3-oxathiolan-5-yl]-2(1H)-pyrimidinone (Compound 5)

($R_3$=H, q=1, n=5, r=0, $R_1$=BOC) from $\underline{5}$a (method B).

$^1$H-NMR (DMSO); 7.68 (d, 1H, $J_{HH}$=7.5 Hz, C$\underline{H}$=CH); 7.35–7.17 (m, 5H, Ar); 6.25–6.19 (m, 1H, N—CH—O); 5.75 (d, 1H, CH=C$\underline{H}$); 5.36–5.32 (m, 1H, S—CH—O); 4.44–4.27 (m, 4H, $CH_2$—Ar and COO$CH_2$); 3.49–3.03 (m, 4H, $CH_2$—S and $CH_2$—N); 2.31 (t, 2H, $J_{HH}$=7.20 Hz, $CH_2$—COO); 1.57–1.11 [m, 15H, $CH_2$—(C$\underline{H}_2$)$_3$—$CH_2$ and t.Bu].

Mass (ionization TSP/DI$^+$): 533 [M+H]$^+$ (±)-4-Amino-1-[2-[6-[N-tert-butoxycarbonyl-N-(3trifluoromethylphenyl)methyl-amino]-hexanoyloxymethyl-]1,3-oxathiolan-5-yl]-2(1H)-pyrimidinone (Compound 6)

($R_3$=3-$CF_3$, q=1, n=5, r=0, $R_1$=BOC) from $\underline{5}$b (method A).

Rf=0.05 (AcOEt)

$^1$H-NMR ($CDCl_3$): 1.13–1.73 (m, 15H, 3$CH_2$ and t.Bu); 2.34 (t, 2H, J=7.4 Hz, $CH_2CO$); 3.03–3.17 (m, 3H, $CH_2N$ and H-2'a or H-2'b); 3.47–3.56 (m, 1H, H-2'a or H-2'b); 4.32–4.56 (m, 4H, $CH_2Ph$ and 2H-5'); 5.31 (pseudo q, 1H, $J_1$=3.3 Hz, $J_2$=5.2 Hz, H-4'); 5.83 (t, 1H, J=7.5 Hz, H-5); 6.32 (t, 1H, J=4.8 Hz, H-1'); 7.39–7.68 (m, 4H, H arom.); 7.72 (d, 1H, J=7.53 Hz, H-6).

(±)-4-Amino-1-[2-[6-[N-tert-butoxycarbonyl-N-(2-trifluoromethyl-phenyl)methyl-amino]-hexanoyloxymethyl-]-1,3-oxathiolan-5-yl]-2(1H)-pyrimidinone (Compound 7)

($R_3$=2-$CF_3$, q=1, n=5, r=0, $R_1$=BOC) from $\underline{5}$c (method A).

Rf=0.05 (AcOEt)

$^1$H-NMR ($CDCl_3$): 1.18–1.68 (m, 15H, 3$CH_2$ and t.Bu); 2.35 (t, 2H, J=7.4 Hz, $CH_2CO$); 3.05–3.23 (m, 3H, $CH_2N$ and H-2'a or H-2'b); 3.49–3.73 (m, 1H, H-2'a or H-2'b); 3.43–4.82 (m, 4H, $CH_2Ph$ and 2H-5'); 5.30–5.35 (m, 1H, H-4'); 6.33 (t, 1H, J=4.6 Hz, H-1'); 7.26–7.84 (m, 5H, H arom. and H-6).

(±)-4-Amino-1-[2-[6-[6-[N'-tert-butoxycarbonyl-N'-(2-trifluoromethylphenyl)methylamino]-N-tert-butoxycarbonyl-hexylamino]-hexanoyloxymethyl]-1,3-oxathiolan-5-yl]-2(1H)-pyrimidinone (Compound 8)

($R_3$=2-$CF_3$, q=1, n=6, r=1, m=5, $R_1$=$R_2$=BOC) from $\underline{10}$b (method A).

Rf=0.05 (AcOEt)

$^1$H-NMR ($CDCl_3$): 1.10–1.74 (m, 32H, 7$CH_2$ and 2t.Bu); 2.37 (t, 2H, J=7.4 Hz, $CH_2CO$); 3.10–3.23 (m, 5H, 2$CH_2N$ and H-2'a or H-2'b); 3.51–3.64 (m, 1H, H-2'a or H-2'b); 4.35–4.43 (m, 1H, H-5'a or H-5'b); 4.52–4.64 (m, 3H, $CH_2Ph$ and H-5'a or H-5'b); 5.34 (q, 1H, $J_1$=3.1 Hz, $J_2$=4.7 Hz, H-4'); 5.85 (bs, 1H, H-5); 6.34 (pseudo t, 1H, H-1'); 7.26–7.64 (m, 5H, H arom. and H-5); 7.78 (d, 1H, J=7.2 Hz, H-6).

(±)-4-Amino-1-[2-[6-(N-ethoxycarbonyl-N-phenylmethylamino)-hexanoyloxymethyl]-1,3-oxathiolan-5-yl]-2(1H)-pyrimidinone (Compound 9)

($R_3$=H, q=1, n=5, r=0, $R_1$=EtOCO) from $\underline{5}$"a (method A).

Rf=0.05 (AcOEt)

$^1$H-NMR ($CDCl_3$): 1.10–1.60 (m, 9H, 3$CH_2$ and $CH_3$); 2.25 (t, 2H, J=7.5 Hz, $CH_2CO$); 2.90–3.20 (m, 3H, $CH_2N$ and H-2'a or H-2'b); 3.40–3.50 (m, 1H, H-2'a or H-2'b); 4.00–4.20 (m, 2H, C$\underline{H}_2CH_3$); 4.25–4.50 (m, 4H, $CH_2Ph$ and 2H-5'); 5.20–5.25 (m, 1H, H-4'); 5.70–5.85 (m, 1H, H-5); 6.20–6.30 (m, 1H, H-1'); 7.05–7.25 (m, 5H, H arom.); 7.50–7.65 (m, 1H, H-6).

(±)-4-Amino-1-[2-[(N-tert-butoxycarbonyl-N-phenylmethylamino)-acetyloxymethyl]-1,3-oxathiolan-5-yl]-2(1H)-pyrimidinone (Compound 10)

($R_3$=H, q=1, n=1, r=0, $R_1$=BOC) from $\underline{5}$g (method A).

Rf=0.05 (AcOEt)

$^1$H-NMR ($CDCl_3$): 1.40 (m, 9H, t.Bu); 2.90–3.00 (m, 1H, H-2'a or H-2'b); 3.35–3.45 (m, 1H, H-2'a or H-2'b);

3.75–3.90 (m, 2H, CH$_2$N); 4.20–4.55 (m, 5H, CH$_2$Ph and 2H-5'); 5.15–5.25 (m, 1H, H-4'); 5.70–5.80 (m, 1H, H-5); 6.20–6.30 (q, 1H, J$_1$=5.0 Hz, J$_2$=10.0 Hz, H-1'); 7.10–7.30 (m, 5H, H arom.); 7.45–7.55 (m, 1H, H-6).

(±)-4-amino-1-[2-[4-(N-tert-butoxycarbonyl-N-phenylmethylamino)-butanoyloxymethyl]-1,3-oxathiolan-5-yl]-2(1H)-pyrimidinone (Compound 11)

(R$_3$=H, q=1, n=3, r=0, R$_1$=BOC) from 5e (method B).

$^1$H-NMR (CDCl$_3$): 7.72 (d, 1H, J$_{HH}$=7.5 Hz, C$\underline{H}$=CH); 7.34–7.15 (m, 5H, Ar); 6.33–6.28 (m, 1H, N—CH—O); 5.80 (bs, 1H, CH=C$\underline{H}$); 5.33–5.38 (m, 1H, S—CH—O); 4.56–4.32 (m, 4H, CH$_2$—Ar and COOCH$_2$); part AB of an ABX system; VA=3.51, VB=3.08, JAB=12.2 Hz, JAX=5.3 Hz, JBX=4.0 Hz, CH$_2$S; 3.28–3.14 (m, 2H, CH$_2$—CH$_2$—N); 2.34 (t, 2H, J$_{HH}$=7.5 Hz, CH$_2$COO); 1.90–1.75 (m, 2H, CH$_2$—C$\underline{H}_2$—CH$_2$); 1.43 (s, 9H, t.Bu).

Mass (ionization TSP/DI$^+$); 550 [M+H]$^+$, 527 [M+Na]$^+$ (±)-4-Amino-1-[2-[6-[4-(N'-tert-butoxycarbonyl-N'-phenylmethylamino)-N-tert-butoxycarbonyl-butylamino]-hexanoyloxymethyl]-1,3-oxathiolan-5-yl]-2(1H)-pyrimidinone (Compound 12)

(R$_3$=H, q=1, n=4, r=1, m=5, R$_1$=R$_2$=BOC) from 10g (method B).

$^1$H-NMR (CDCl$_3$): 7.77 (d, 1H, J$_{HH}$=7.5 Hz, C$\underline{H}$=CH); 7.33–7.17 (m, 5H, Ar); 6.37 (bs, 2H, NH$_2$); 6.34–6.29 (m, 1H, N—CH—O); 5.85 (bs, 1H, CH=C$\underline{H}$); 5.34–5.30 (m, 1H, S—CH—O); 4.60–4.33 (m, 4H, CH$_2$—Ar and COOCH$_2$); 3.58–3.06 (m, 6H, Ar—CH$_2$—N—C$\underline{H}_2$ and C$\underline{H}_2$—N—C$\underline{H}_2$); 2.35 (t, 2H, J$_{HH}$=7.4 Hz, CH$_2$COO); 1.71–1.21 [m, 28H, CH$_2$—(C$\underline{H}_2$)$_3$—CH$_2$—N and 2t.Bu].

Mass (ionization TSP/DI$^+$): 704 [M+H]$^+$, 726 [M+Na]$^+$, 459

(±)-4-Amino-1-[2-[6-[3-(N'-tert-butoxycarbonyl-N'-phenylmethylamino)-N-tert-butoxycarbonyl-propylamino]-hexanoyloxymethyl]-1,3-oxathiolan-5-yl]-2(1H)-pyrimidinone (Compound 13)

(R$_3$=H, q=1, n=3, r=1, m=5, R$_1$=R$_2$=BOC) from 10f (method B).

$^1$H-NMR (DMSO): 7.68 (d, 1H, C$\underline{H}$=CH); 7.39–7.17 (m, 5H, Ar); 6.25–6.19 (m, 1H, N—CH—O); 5.73 (d, 1H, CH=C$\underline{H}$); 5.36–5.32 (m, 1H, S—CH—O); 4.45–4.27 (m, 4H, CH$_2$—Ar and COOCH$_2$); 3.48–2.98 (m, 8H, CH$_2$—S and 3CH$_2$—NCOO); 2.34 (t, 2H, CH$_2$COO); 1.65–1.13 [m, 26H, CH$_2$—(C$\underline{H}_2$)$_3$—CH$_2$, CH$_2$—C$\underline{H}_2$—CH$_2$ and t.Bu].

Mass (ionization TSP/DI$^+$): 690 [M+H]$^+$, 712 [M+Na]$^+$, 252 [230+Na]$^+$ (±)-4-Amino-1-[2-[5-[3(N'-tert-butoxycarbonyl-N'-phenylmethylamino)-N-tert-butoxycarbonyl-propylamino]-pentanoyloxymethyl]-1,3-oxathiolan-5-yl]-2(1H)-pyrimidinone (Compound 14)

(R$_3$=H, q=1, n=3, r=1, m=4, R$_1$=R$_2$=BOC) from 10h (method 13).

$^1$H-NMR (CDCl$_3$): 7.92–7.70 (bs, 1H, C$\underline{H}$=CH); 7.35–7.15 (m, 5H, Ar); 6.33–6.29 (m, 1H, N—CH—O); 6.42 (bsd, 2H, NH$_2$); 5.98–5.80 (bs, 1H, CH=C$\underline{H}$); 5.35–5.30 (m, 1H, CH—S); 4.64–4.35 (m, 4H, CH$_2$—Ar and CH$_2$O); 3.60–3.00 (m, 8H, CH$_2$—S and 3CH$_2$—NCOO); 2.42–2.33 (m, 2H, CH$_2$COO); 1.70–1.33 [m, 24H, CH$_2$—(C$\underline{H}_2$)$_2$—CH$_2$, CH$_2$—C$\underline{H}_2$—CH$_2$ and t.Bu].

Mass (ionization TSP/DI$^+$): 676 [M+H]$^+$, 576 [676-BOC]$^+$, 459

(2S,5R)-4-Amino-1-[2-[5-[5-(N'-tert-butoxycarbonyl-N'-phenylmethylamino)-N-tert-butoxycarbonyl-pentylamino]-pentanoyloxymethyl]-1,3-oxathiolan-5-yl]-2(1H)-pyrimidinone (Compound 15)

(R$_3$=H, q=1, n=5, r=1, m=4, R$_1$=R$_2$=BOC) from 10d (method B).

$^1$H-NMR (CDCl$_3$): 7.82–7.60 (bs, 1H, C$\underline{H}$=CH); 7.35–7.12 (m, 5H, Ar); 6.33–6.29 (m, 1H, N—CH—O); 5.95–5.75 (bd, 1H, CH=C$\underline{H}$); 5.35–5.28 (m, 1H, CH—S); 4.60–4.30 (m, 4H, CH$_2$—Ar and CH$_2$O); 3.55–3.00 (m, 8H, CH$_2$—S and 3CH$_2$—NCOO); 2.41–2.30 (m, 2H, CH$_2$COO); 1.70–1.10 [m, 28H, CH$_2$—(C$\underline{H}_2$)$_3$—CH$_2$, CH$_2$—(C$\underline{H}_2$)$_2$—CH$_2$ and t.Bu].

Mass (ionization TSP/DI$^+$): 704 [M+H]$^+$, 726 [M+Na]$^+$ (±)-4-Amino-1-[2-[3-[5-(N'-tert-butoxycarbonyl-N'-phenylmethylamino)-N-tert-butoxycarbonyl-pentylamino]-pentanoyloxymethyl]-1,3-oxathiolan-5-yl]-2(1H)-pyrimidinone (Compound 16)

(R$_3$=H, q=1, n=5, r=1, m=2, R$_1$=R$_2$=BOC) from 10i (method B).

$^1$H-NMR (CDCl$_3$): 7.71 (bs, 1H, C$\underline{H}$=CH); 7.35–7.12 (m, 5H, Ar); 6.33–6.29 (m, 1H, N—CH—O); 5.88–5.80 (bd, 1H, CH=C$\underline{H}$); 5.35–5.30 (m, 1H, CH—S); 4.60–4.30 (m, 4H, CH$_2$—Ar and CH$_2$O); 3.60–3.00 (m, 8H, CH$_2$—S and 3CH$_2$—NCOO); 2.65–2.54 (m, 2H, CH$_2$COO); 1.60–1.10 [m, 24H, CH$_2$—(C$\underline{H}_2$)$_3$—CH$_2$ and t.Bu].

Mass (ionization TSP/DI$^+$): 676 [M+H]$^+$, 698 [M+C$_3$H$_7$]$^+$, 459, 252 [230+Na]$^+$ (±)-4-Amino-1-[2-[5-(N-tert-butoxycarbonyl-N-phenylmethylamino)-pentanoyloxymethyl]-1,3-oxathiolan-5-yl]-2(1H)-pyrimidinone (Compound 17)

(R$_3$=H, q=1, n=4, r=0, R$_1$=BOC) from 5d (method B).

$^1$H-NMR (CDCl$_3$): 7.89–7.65 (bs, 1H, C$\underline{H}$=CH); 7.35–7.15 (m, 5H, Ar); 6.35–6.30 (m, 1H, N—CH—O); 5.95–5.70 (bs, 1H, CH=C$\underline{H}$); 5.33–5.29 (m, 1H, CHS); 4.60–4.33 (m, 4H, CH$_2$—Ar and OCH$_2$); 3.58–3.02 (m, 4H, CH$_2$S and C$\underline{H}_2$—NCOO); 2.41–2.30 (m, 2H, CH$_2$COO); 1.70–1.35 [m, 13H, CH$_2$—(C$\underline{H}_2$)$_2$—CH$_2$ and t.Bu].

Mass (ionization TSP/DI$^+$): 519 [M+H]$^+$ (±)-4-Amino-1-[2-[6-[5-(N'-acetyl-N'-phenylmethylamino)-N-acetyl-pentylamino]-hexanoyloxymethyl]-1,3-oxathiolan-5-yl]-2(1H)-pyrimidinone (Compound 18)

(R$_3$=H, q=1, n=5, r=1, m=5, R$_1$=R$_2$=Ac) from 10"a (method B).

$^1$H-NMR (DMSO): 7.69 (d, 1H, C$\underline{H}$=CH); 7.40–7.15 (m, 5H, Ar); 6.25–6.18 (m, 1H, N—CH—O); 5.78–5.72 (m, 1H, CH=C$\underline{H}$); 5.39–5.31 (m, 1H, S—CH—O); 4.55–4.26 (m, 4H, CH$_2$—Ar and COOCH$_2$); 3.48–3.05 (m, 8H, CH$_2$—S and 3CH$_2$—NCOO); 2.40–2.27 (m, 2H, CH$_2$COO); 2.10–1.90 (3s, 6H, 2COCH$_3$); 1.60–1.05 [m, 12H, CH$_2$—(CH$_2$)$_3$—CH$_2$ and CH$_2$—(CH$_2$)$_3$—CH$_2$].

Mass (ionization TSP/DI$^+$): 602 [M+H]$^+$, 624 [M+Na]$^+$, 459

(±)-4-Amino-1-[2-[6-[5-[N'-(2,2-Dimethylpropionyl))-N'-phenylmethylamino]-N-(2,2-dimethylpropionyl)-pentylamino]-hexanoyloxymethyl]-1,3-oxathiolan-5-yl]-2(1H)-pyrimidinone (Compound 19)

(R$_3$=H, q=1, n=5, r=1, m=5, R$_1$=R$_2$=Piv) from 10"b (method B).

$^1$H-NMR (CDCl$_3$): 7.81 (d,=CH—N—CO); 7.38–7.12 (m, 5H, Ar); 6.37–6.30 (m, 1H, N—CH—O); 5.91 (m, 1H, CH=C$\underline{H}$N); 5.36–5.31 (m, 1H, CHS); 4.69–4.61 (s, 2H, CH$_2$—Ar) 4.61–4.35 (m, 2H, COOCH$_2$); 3.60–3.10 (m, 8H, CH$_2$—S and 3CH$_2$—N); 2.38 (t, 2H, CH$_2$CO); 1.75–1.10 [m, 30H, 2CH$_2$—(C$\underline{H}_2$)$_3$—CH$_2$ and 2t.Bu].

Mass (ionization TSP/DI$^+$): 686 [M+H]$^+$, 708 [M+Na]$^+$, 1372 [2M+H]$^+$ (±)-4-Amino-1-[2-[5-[6-(N'-tert-butoxycarbonyl-N'-phenylmethylamino)-N-tert-butoxycarbonyl-hexylamino]-pentanoyloxymethyl]-1,3-oxathiolan-5-yl]-2(1H)-pyrimidinone (Compound 20)

(R$_3$=H, q=1, n=6, r=1, m=4, R$_1$=R$_2$=BOC) from 10e (method A). which was directly used in the subsequent reaction.

Compounds of formula I-B (±)-1-(2-Hydroxymethyl-1,3-oxathiolan-5-yl)-4-[[6-(N'-phenylmethoxycarbonyl-N'-phenylmethylamino)-N-phenylmethoxycarbonyl-hexylamino]-acetylamino]-2(1H)-pyrimidinone (Compound 21)

($R_3$=H, q=1, n=6, r=1, m=1, $R_1$=$R_2$=BzOCO) from 10n (method A)

$^1$H-NMR (CDCl$_3$): 1.00–1.45 (m, 8H, 4CH$_2$); 2.95–3.30 (m, 5H, 2CH$_2$N and H-2'a or H-2'b); 3.40–3.45 (m, 1H, H-2'a or H-2'b); 3.75–4.10 (m, 4H, CH$_2$CO and 2H-5'); 4.35 (bs, 2H, CH$_2$Ph); 5.05 (bs, 4H, 2CH$_2$O); 5.20 (pseudo t, 1H, H-4'); 6.20 (pseudo q, 1H, H-1'); 7.00–7.30 (m, 16H, H arom. and H-5); 8.30 (d, 1H, J=7.5 Hz, H-6), 9.35 (bs, 1H, NHCO).

(±)-1-(2-Hydroxymethyl-1,3-oxathiolan-5-yl)-4-[[6-[N'-tert-butoxycarbonyl-N'-(4-methoxyphenyl)methylamino]-N-tert-butoxycarbonyl-hexylamino]-acetylamino]-2(1H)-pyrimidinone (Compound 22)

($R_3$=4-OCH$_3$, q=1, n=6, r=1, m=1, $R_1$=$R_2$=BOC) from 10l (method A)

Rf=0.2 (AcOEt)

$^1$H-NMR (CD$_3$OD): 1.30–1.60 (m, 26H, 4CH$_2$ and 2t.Bu); 3.05–3.35 (m, 5H, 2CH$_2$N and H-2'a or H-2'b); 3.60–3.70 (m, 1H, H-2'a or H-2'b); 3.80 (s, 3H, CH$_3$); 3.95–4.30 (m, 4H, CH$_2$CO and 2H-5'); 4.35 (bs, 2H, CH$_2$Ph); 5.35 (pseudo t, 1H, H-4'); 6.35 (pseudo q, 1H, H-1'); 6.80–7.30 (m, 4H, H arom.); 7.40 (d, 1H, J=7.5 Hz, H-5); 8.45 (d, 1H, J=7.5 Hz, H-6); 9.05 (bs, 1H, NHCO).

(±)-1-(2-Hydroxymethyl-1,3-oxathiolan-5-yl)-4-[6-[5-(N'-tert-butoxycarbonyl-N'-phenylmethylamino)-N-tert-butoxycarbonyl-pentylamino]-hexanoylamino]-2(1H)-pyrimidinone (Compound 23)

($R_3$=H, q=1, n=5, r=1, m=5, $R_1$=$R_2$=BOC) from 10c (method A)

Rf=0.36 (CH$_2$Cl$_2$:CH$_3$OH=9:1)

$^1$H-NMR (CDCl$_3$): 1.10–1.76 (m, 30H, 6CH$_2$ and 2t.Bu), 2.44 (t, 2H, J=7.3 Hz, CH$_2$CO); 3.11–3.25 (m, 7H, CH$_2$N and H-2'a or H-2'b); 3.57–3.66 (m, 1H, H-2'a or H-2'b); 3.91–4.17 (m, 2H, 2H-5'); 4.40 (bs, 2H, CH$_2$Ph); 5.33 (pseudo t, 1H, H-4'); 6.32 (pseudo q, 1H, H-1'); 7.18–7.35 (m, 5H, H arom.); 7.41 (d, 1H, J=7.5 Hz, H-5); 8.41 (d, 1H, J=7.5 Hz, H-6); 8.98 (bs, 1H, NHCO).

(±)-1(2-Hydroxymethyl-1,3-oxathiolan-5-yl)-4-[6-4-(N'-tert-butoxycarbonyl-N'-phenylmethylamino)-N-tert-butoxycarbonyl-butylamino]-hexanoylamino]-2(1H)-pyrimidinone (Compound 24)

($R_3$=H, q=1, n=4, r=1, m=5, $R_1$=$R_2$=BOC) from 10g (method A)

$^1$H-NMR (CDCl$_3$): 1.15–1.75 (m, 28H, 5CH$_2$ and 2t.Bu); 2.35–2.60 (t, 2H, J=7.0 Hz, CH$_2$CO); 3.00–3.25 (m, 13H, 6CH$_2$N and H-2'a or H-2'b); 3.50–3.65 (m, 1H, H-2'a or H-2'b); 3.85–4.20 (m, 2H, 2H-5'); 4.40 (bs, 2H, CH$_2$Ph); 5.30 (pseudo t, 1H, H-4'); 6.30 (pseudo t, 1H, H-1'), 7.15–7.35 (m, 5H, H arom.); 7.45 (d, 1H, J=7.5 Hz, H-5); 8.45 (d, 1H, J=7.5 Hz, H-6); 9.45 (bs, 1H, NHCO).

(±)-1-(2-Hydroxymethyl-1,3-oxathiolan-5-yl)-4-[6-[6-(N'-tert-butoxycarbonyl-N'-phenylmethylamino)-N-tert-butoxycarbonyl-hexylamino]-hexanoylamino]-2(1H)-pyrimidinone (Compound 25)

($R_3$=H, q=1, n=6, r=1, m=5, $R_1$=$R_2$=BOC) from 10a (method A)

Rf=0.23 (AcOEt)

$^1$H-NMR (CDCl$_3$): 1.05–1.86 (m, 32H, 7CH$_2$— and 2t.Bu); 2.11–2.41 (m, 4H, CH$_2$CO); 2.87–3.16 (m, 7H, 3CH$_2$N and H-2'a or H-2'b); 3.53–3.62 (m, 1H, H-2'a or H-2'b); 4.34–4.41 (m, 3H, CH$_2$Ph and H-5'a or H-5'b); 4.52–4.61 (m, 1H, H-5'a or H-5'b); 5.32 (pseudo d, 1H, H-4'); 6.25 (pseudo d, 1H, H-1'); 7.12–7.29 (m, 5H, H arom.); 7–40 (d, 1H, J=7.5 Hz, H-5); 8.10 (d, 1H, J=7.5 Hz, H-6), 9.00 (bs, 1H, NHCO).

(±)-1-(2-Hydroxymethyl-1,3-oxathiolan-5-yl)-4-[6-[6[-N'-tert-butoxycarbonyl-N'-(2-trifluoromethylphenyl)methylamino]-N-tert-butoxycarbonyl-hexylamino]-hexanoylamino]-2(1H)-pyrimidinone (Compound 26)

($R_3$=2-CF$_3$, q=1, n=6, r=1, m=5, $R_1$=$R_2$=BOC) from 10b (method A)

Rf=0.4 (AcOEt)

$^1$H-NMR (CDCl$_3$): 1.17–1.69 (m, 32H, 7CH$_2$— and 2t.Bu); 2.45 (t, 2H, J=7.1 Hz, CH$_2$CO); 3.10–3.23 (m, 5H, 2CH$_2$N and H-2'a or H-2'b); 3.55–3.64 (m, 1H, H-2'a or H-2'b); 3.90–4.15 (m, 2H, 2H-5'); 4.57–4.62 (m, 2H, CH$_2$Ph); 5.33 (t, 1H, J=2.9 Hz H-4'); 6.30 (q, 1H, $J_1$=3.3 Hz, $J_2$=5.0 Hz, H-1'); 7.26–7.63 (m, 5H, H arom. and H-5); 8.42 (d, 1H, J=7.5 Hz, H-6); 9.27 (bs, 1H, NHCO).

(±)1-(2-Hydroxymethyl-1,3-oxathiolan-5-yl)-4-[6-(N-tert-butoxycarbonyl-N -phenylmethylamino)-hexanoylamino]-2(1H)-pyrimidinone (Compound 27)

($R_3$=H, q=1, n=5, r=0, $R_1$=BOC) from 5a (method A)

Rf=0.52 (AcOEt)

$^1$H-NMR (CDCl$_3$): 1.12–1.67 (m, 15H, 3CH$_2$— and t.Bu); 2.34 (t, 2H, J=7.5 Hz, CH$_2$CO); 3.06–3.13 (m, 3H, CH$_2$N and H-2'a or H-2'b); 3.54—3.54 (m, 1H, H-2'a or H-2'b); 3.80–4.06 (m, 2H, 2H-5'); 4.30 (bs, 2H, CH$_2$Ph); 5.22 (t, 1H, J=3.0 Hz, H-4'); 6.22 (pseudo q, 1H, $J_1$=3.2 Hz, $J_2$=5.1 Hz, H-1'); 7.08–7.25 (m, 5H, H arom.); 7.33 (d, 1H, J=7.5 Hz, H-5); 8.33 (d, 1H, J=7.5 Hz, H-6); 9.62 (bs, 1H, NHCO).

(±)1-(2-Hydroxymethyl-1,3-oxathiolan-5-yl)-4-[6-[N-tert-butoxycarbonyl-N-(3-trifluoromethylphenyl)methylamino]-hexanoylamino]-2(1H)-pyrimidinone (Compound 28)

($R_3$=3-CF$_3$, q=1, n=5, r=0, $R_1$=BOC) from 5b (method A)

Rf=0.23 (AcOEt)

$^1$H-NMR (CDCl$_3$): 1.12–1.69 (m, 15H, 3CH$_2$— and t.Bu); 2.43 (m, 2H, J=7.3 Hz, CH$_2$CO); 3.15–3.23 (m, 3H, CH$_2$N and H-2'a or H-2'b); 3.54–3.63 (m, 1H, H-2'a or H-2'b); 3.81–4.15 (m, 2H, 2H-5'); 4.41 (bs, 2H, CH$_2$Ph); 5.31 (t, 1H, J=2.8 Hz, H-4'); 6.30 (pseudo q, 1H, $J_1$=3.1 Hz, $J_2$=5.0 Hz, H-1'); 7.38–7.68 (m, 5H, H arom. and H-5); 8.40 (d, 1H, J=7.5 Hz, H-6); 9.37 (bs, 1H, NHCO).

(±) 1-(2-Hydroxymethyl-1,3-oxathiolan-5-yl)-4-[6-[N-tert-butoxycarbonyl-N-(2-trifluoromethylphenyl)methylamino]-hexanoylamino]-2(1H)-pyrimidinone (Compound 29)

($R_3$=2-CF$_3$, q=1, n=5, r=0, $R_1$=BOC) from 5c (method A)

Rf=0.4 (AcOEt)

$^1$H-NMR (CDCl$_3$): 1.18–1.68 (m, 15H, 3CH$_2$— and t.Bu); 2.43 (t, 2H, J=7.3 Hz, CH$_2$CO); 3.16–3.24 (m, 3H, CH$_2$N and H-2'a or H-2'b); 3.56–3.64 (m, 1H, H-2'a or H-2'b); 3.90–4.16 (m, 2H, 2H-5'); 4.58–4.63 (m, 2H, CH$_2$Ph); 5.33 (t, 1H, J=3.0 Hz, H-4'); 6.30 (q, 1H, $J_1$=3.4 Hz, $J_2$=5.0 Hz, H-1'); 7.26–7.63 (m, 5H, H arom. and H-5); 8.39 (d, 1H, J=7.5 Hz, H-6); 9.24 (bs, 1H, NHCO).

(±)1-(2-Hydroxymethyl-1,3-oxathiolan-5-yl)-4-[6-(N-ethoxycarbonyl-N-phenylmethylamino)-hexanoylamino]-2(1H)-pyrimidinone (Compound 30)

($R_3$=H, q=1, n=5, r=0, $R_1$=EtOCO) from 5''a (method A)

Rf=0.2 (AcOEt)

$^1$H-NMR (CDCl$_3$): 1.10–1.70 (m, 9H, 3CH$_2$— and CH$_3$); 2.05–2.45 (m, 3H, 2CH$_2$CO and OH); 3.00–3.20 (m, 3H, CH$_2$N and H-2'a or H-2'b); 3.45–3.60 (m, 1H, H-2'a or H-2'b); 3.80–3.90 (m, 1H, H-5'a or H'-5b); 3.95–4.20 (m, 3H, C$\underline{H}_2$CH$_3$ and H-5'a or H-5'b); 4.30–4.45 (bs, 2H, CH$_2$Ph); 5.25–5.30 (m, 1H, H-4'); 6.20–6.30 (m, 1H, H-1');

7.05–7.30 (m, 5H, H arom.); 7.35 (d, 1H, J=7.5 Hz, H-5); 8.30 (d, 1H, J=7.5 Hz, H-6), 9.40 (bs, 1H, NH).

(±)1-(2-Hydroxymethyl-1,3-oxathiolan-5-yl)-4-[(N-tert-butoxycarbonyl-N-phenylmethylamino)-acetylamino]-2(1H)-pyrimidinone (Compound 31)

($R_3$=H, q=1, n=1, r=0, $R_1$=BOC) from 5g (method A)

Rf=0.35 (AcOEt)

$^1$H-NMR (CDCl$_3$): 1.40 (m, 9H, t.Bu); 3.10–3.20 (m, 1H, H-2'a or H-2'b); 3.45–3.55 (m, 1H, H-2'a or H-2'b); 3.80–4.10 (m, 4H, CH$_2$N and 2H'-5); 4.45 (bs, 2H, CH$_2$Ph); 5.20–5.25 (m, 1H, H-4'); 6.10–6.15 (m, 1H, H-1'); 7.10–7.30 (m, 6H, H arom. and H-5); 8.30 (d, 1H, J=7.4 Hz, H-6).

(±)-1-(2Hydroxymethyl-1,3-oxathiolan-5-yl)-4-[5-[6-(N'-tert-butoxycarbonyl-N'-phenylmethylamino)-N-tert-butoxycarbonyl-hexylamino]-pentanoylamino]-2(1H)-pyrimidinone (Compound 32)

($R_3$=H, q=1, n=6, r=1, m=4, $R_1$=$R_2$=BOC) from 10e (method A) which was directly used in the subsequent reaction.

(±)-1-(2-Hydroxymethyl-1,3-oxathiolan-5-yl)-4-[6-[3-(N'-tert-butoxycarbonyl-N'-phenylmethylamino)-N-tert-butoxycarbonyl-propylamino]-hexanoylamino]-2(1H)-pyrimidinone (Compound 33)

($R_3$=H, q=1, n=3, r=1, m=5, $R_1$=$R_2$=BOC) from 10f (method A) which was directly used in the subsequent reaction.

(±)-1-(2-Hydroxymethyl-1,3-oxathiolan-5-yl)-4-[5-[5-(N'-tert-butoxycarbonyl-N'-phenylmethylamino)-N-tert-butoxycarbonyl-pentylamino]-pentanoylamino]-2(1H)-pyrimidinone (Compound 34)

($R_3$=H, q=1, n=5, r=1, m=4, $R_1$=$R_2$=BOC) from 10d (method A) which was directly used in the subsequent reaction.

Compounds of formula I-C (±)-4-[[6-(N'-Phenylmethoxycarbonyl-N'-phenylmethylamino)-N-phenylmethoxycarbonyl-hexylamino]-acetylamino]-1-[2-[[6-(N'-phenylmethoxycarbonyl-N'-phenylmethylamino)-N-phenylmethoxycarbonyl-hexylamino]-acetoxymethyl]-1,3-oxathiolan-5-yl]-2(1H)-pyrimidinone (Compound 35)

($R_3$=H, q=1, n=6, r=1, m=1, $R_1$=$R_2$=BzOCO) from 10n (method A)

$^1$H-NMR (CDCl$_3$): 1.10–1.45 (m, 16H, 8CH$_2$); 3.00–3.30 (m, 9H, 4CH$_2$N and H-2'a or H-2'b); 3.40–3.55 (m, 1H, H-2'a or H-2'b); 3.85–4.05 (m, 5H, 2CH$_2$CO and H-5'a or H-5'b); 4.30–4.50 (m, 5H, 2CH$_2$Ph and H-5'a or H-5'b); 5.00 (bs, 8H, 4CH$_2$O); 5.20 (pseudo t, 1H, H-4'); 6.15 (pseudo q, 1H, H-1'); 7.00–7.30 (m, 3H, H arom. and H-5); 7.95 (d, 1H, J=7.5 Hz, H-6); 9.00 (bs, 1H, NHCO).

(±)-4-[6-[6-(N'-tert-Butoxycarbonyl-N'-phenylmethylamino)-N-tert-butoxycarbonyl-hexylamino]-hexanoylamino]-1-[2-[6-[6-(N'-tert-butoxycarbonyl-N'-phenylmethylamino)-N-tert-butoxycarbonyl-hexylamino]-hexanoyloxymethyl]-1,3-oxathiolan-5-yl]-2(1H)-pyrimidinone (Compound 36)

($R_3$=H, q=1, n=6, r=1, m=5, $R_1$=$R_2$=BOC) from 10a (method A)

$^1$H-NMR (CDCl$_3$): 1.06–1.80 (m, 64H, 14CH$_2$ and 4t.Bu); 2.28–2.41 (m, 4H, 2CH$_2$CO); 2.95–3.17 (m, 13H, 6CH$_2$N and H-2'a or H-2'b); 3.52–3.61 (m, 1H, H-2'a or H-2'b); 4.34–4.41 (m, 5H, 2CH$_2$Ph and H-5'a or H-5'b); 4.52–4.61 (m, 1H, H-5'a or H-5'b); 5.32 (pseudo d, 1H, H-4'); 6.25 (pseudo d, 1H, H-1'); 7.13–7.34 (m, 10H, H arom.); 7.38 (d, 1H, J=7.5 Hz, H-5); 8.04 (d, 1H, J=7.5 Hz, H-6); 8.90 (bs, 1H, NHCO).

(±)-4-[6-[5-(N'-tert-Butoxycarbonyl-N'-phenylmethylamino)-N-tert-butoxycarbonyl-pentylamino]-hexanoylamino]-1-[-6-[5-(N'-tert-butoxycarbonyl-N'-phenylmethylamino)-N-tert-butoxycarbonyl-pentylamino]-hexanoyloxymethyl]-1,3-oxathiolan-5-yl]-2(1H)-pyrimidinone (Compound 37)

($R_3$=H, q=1, n=5, r=1, m=5, $R_1$=$R_2$=BOC) from 10c (method A)

Rf=0.75 (AcOEt)

$^1$H-NMR (CDCl$_3$): 1.09–1.77 (m, 60H, 12CH$_2$ and 4t.Bu); 2.40 (q, 4H, $J_1$=7.0 Hz, $J_2$=13.0 Hz, CH$_2$CO); 2.99–3.24 (m, 13H, 6CH$_2$N and H-2'a or H-2'b); 3.58–3.67 (m, 1H, H-2'a or H-2'b); 4.40–4.46 (m, 5H, 2CH$_2$Ph and H-5'a or H-5'b); 4.58–4.67 (m, 1H, H-5'a or H-5'b); 5.38 (pseudo t, 1H, H-4'), 6.31 (pseudo q, 1H, H-1'); 7.23–7.36 (m, 10H, H arom.); 7.43 (d. 1H, J=7.5 Hz, H-5); 8.10 (d, 1H, J=7.5 Hz, H-6).

(±)-4-[6-[4-(N'-tert-Butoxycarbonyl-N'-phenylmethylamino)-N-tert-butoxycarbonyl-butylamino]-hexanoylamino]-1-[2-[6-[4-(N'-tert-butoxycarbonyl-N'-phenylmethylamino)-N-tert-butoxycarbonyl-butylamino]-hexanoyloxymethyl]-1,3-oxathiolan-5-yl]-2(1H)-pyrimidinone (Compound 38)

($R_3$=H, q=1, n=4, r=1, m=5, $R_1$=$R_2$=BOC) from 10g (method A)

$^1$H-NMR (CDCl$_3$): 1.15–1.80 (m, 56H, 10CH$_2$ and 4t.Bu); 2.25–2.50 (m, 4H, 2CH$_2$CO); 3.00–3.30 (m, 13H, 6CH$_2$N and H-2'a or H-2'b); 3.60–3.70 (m, 1H, H-2'a or H-2'b); 4.35–4.50 (bs, 5H, 2CH$_2$Ph and H-5'a or H-5'b); 4.60–4.70 (m, 1H, H-5'a or H-5'b); 5.35 (pseudo t, 1H, H-4'); 6.30 (pseudo t, 1H, H-1'); 7.15–7.40 (m, 10H, H arom.); 7.50 (d, 1H, J=7.5 Hz, H-5); 8.15 (d, 1H, J=7.5 Hz, H-6); 10.25 (bs, 1H, NHCO).

(±)-4-[6-(N-tert-Butoxycarbonyl-N-phenylmethylamino)-hexanoylamino]-1-[2-[6-(N-tert-butoxycarbonyl-N-phenylmethylamino)-hexanoyloxymethyl]-1,3-oxathiolan-5-yl]-2(1H)-pyrimidinone (Compound 39)

($R_3$=H, q=1, n=5, r=0, $R_1$=BOC) from 5a (method A)

Rf=0.7 (AcOEt)

$^1$H-NMR (CDCl$_3$): 1.16–1.68 (m, 30H, 6CH$_2$ and 2t.Bu); 2.18–2.38 (m, 4H, 2CH$_2$CO); 2.88–3.12 (m, 5H, 2CH$_2$N and H-2'a or H-2'b); 3.49–3.58 (m, 1H, H-2'a or H-2'b); 4.34 (bs, 5H, 2CH$_2$Ph and H-5'a or H-5'b); 4.49–4.57 (m, 1H, H-5'a or H-5'b); 5.28 (pseudo q, 1H, $J_1$=3.1 Hz, $J_2$=4.8 Hz, H-4'); 6.22 (pseudo q, 1H, $J_1$=3.0 Hz, $J_2$=5.1 Hz, H-1'); 7.10–7.26 (m, 10H, H arom.); 7.37 (d, 1H, J=7.5 Hz, H-5); 8.03 (d, 1H, J=7.5 Hz, H-6); 9.39 (bs, 1H, NHCO).

(±)-4-[6-[N-tert-Butoxycarbonyl-N-(3-trifluoromethylphenyl)methylamino]-hexanoyl-amino]-1-[2-[6-[N-tert-butoxycarbonyl-N-(3-trifluoromethylphenyl)methylamino]-hexanoyloxymethyl]-1,3-oxathiolan-5-yl]-2(1H)-pyrimidinone (Compound 40)

($R_3$=3-CF$_3$, q=1, n=5, r=0, $R_1$=BOC) from 5b (method A)

Rf=0.5 (AcOEt)

$^1$H-NMR (CDCl$_3$): 1.14–1.76 (m, 30H, 6CH$_2$ and 2t.Bu); 2.32–2.45 (m, 4H, 2CH$_2$CO); 3.16–3.24 (m, 5H, CH$_2$N and H-2'a or H-2'b); 3.57–3.60 (m, 1H, H-2'a or H-2'b); 4.44–4.67 (m, 6H, 2CH$_2$Ph and 2H-5'); 5.37 (pseudo q, 1H, H-4'); 6.29 (pseudo q, 1H, H-1'); 7.40–7.70 (m, 11H, H arom. and H-5); 8.12 (d, 1H, J=7.5 Hz, H-6).

(±)-4-[6-[N-tert-Butoxycarbonyl-N-(2-trifluoromethylphenyl)methylamino]-hexanoyl-amino]-1-[2-[6-[N-tert-butoxycarbonyl-N-(2-trifluoromethylphenyl)methylamino]-hexanoyloxymethyl]-1,3-oxathiolan-5-yl]-2(1H)-pyrimidinone (Compound 41)

($R_3$=2-CF$_3$, q=1, n=5, r=0, $R_1$=BOC) from 5c (method A)

Rf=0.6 (AcOEt)

$^1$H-NMR (CDCl$_3$): 1.16–1.65 (m, 30H, 6CH$_2$ and 2t.Bu); 2.30–2.46 (m, 4H, 2CH$_2$CO); 3.03–3.24 (m, 5H, 2CH$_2$N and H-2'a or H-2'b); 3.58–3.67 (m, 1H, H-2'a or H-2'b); 4.37–4.45 (m, 1H, H-5'a or H-5'b); 4.58–4.64 (m, 5H, 2CH₂Ph and H-5'a or H-5'b); 5.38 (q, 1H, J₁=3.2 Hz, J₂=4.9 Hz, H-4'); 6.32 (q, 1H, J₁=3.0 Hz, J₂=5.4 Hz, H-1'); 7.26–7.64 (m, 9H, H arom. and H-5); 8.12 (d, 1H, J=7.5 Hz, H-6); 8.85 (bs, 1H, NHCO).

(±)-4-[6-[6[-N'-tert-Butoxycarbonyl-N'-(2-trifluoromethylphenyl)methylamino]-N-tert-butoxycarbonyl-hexylamino]-hexanoylamino]-1-[2-[6-[6-[N'-tert-butoxycarbonyl-N'-(2-trifluoromethylphenyl)methylamino]-N-tert-butoxycarbonyl-hexylamino]-hexanoyloxymethyl]-13-oxathiolan-5-yl]-2(1H)-pyrimidinone (Compound 42)

(R₃=2-CF₃, q=1, n=6, r=1, m=5, R₁=R₂=BOC) from 10b (method A)
¹H-NMR (CDCl₃): 1.12–1.73 (m, 64H, 14CH₂ and 4t.Bu); 2.34–2.49 (m, 4H, 2CH₂CO); 3.02–3.22 (m, 9H, 4CH₂N and H-2'a or H-2'b); 3.58–3.67 (m, 1H, H-2'a or H-2'b); 4.37–4.45 (m, 1H, H-5'a or H-5'b); 4.57–4.63 (m, 9H, 4CH₂Ph and H-5'a or H-5'b); 5.38 (q, 1H, J₁=3.2 Hz, J₂=5.0 Hz, H-4'); 6.31 (q, 1H, J₁=3.2 Hz, J₂=5.0 Hz, H-1'); 7.26–7.63 (m, 9H, H arom. and H-5); 8.10 (d, 1H, J=7.5 Hz, H-6); 8.90 (bs, 1H, NHCO).

(±)-4-[6-(N-Ethoxycarbonyl-N-phenylmethylamino)-hexanoylamino]-1-[2-[6-(N-ethoxycarbonyl-N-phenylmethylamino)-hexanoyloxymethyl]-1,3-oxathiolan-5-yl]-2(1H)-pyrimidinone (Compound 43)

(R₃=H, q=1, n=5, r=0, R₁=EtOCO) from 5"a (method A)
¹H-NMR (CDCl₃): 1.10–1.70 (m, 18H, 6CH₂ and 2CH₃); 2.20–2.40 (m, 4H, 2CH₂CO); 3.00–3.20 (m, 5H, 2CH₂N and H-2'a or H-2'b); 3.50–3.60 (m, 1H, H-2'a or H-2'b); 4.05 (q, 4H, J₁=6.9 Hz, J₂=13.9 Hz, 2CH₂CH₃); 4.30–4.45 (m, 5H, 2CH₂Ph and H-5'a or H-5'b); 4.50–4.60 (m, 1H, H-5'a or H-5'b); 5.25–5.35 (m, 1H, H-4'); 6.20–6.31 (m, 1H, H-1'); 7.05–7.25 (m, 10H, H arom.); 7.35 (d, 1H, J=7.5 Hz, H-5); 8.05 (d, 1H, J=7.5 Hz, H-6); 8.75 (bs, 1H, NH).

(±)-4-[(N-Ethoxycarbonyl-N-phenylmethylamino)-acetylamino]-1-[2-[(N-ethoxycarbonyl-N-phenylmethylamino)-acetyloxymethyl]-1,3-oxathiolan-5-yl]-2(1H)-pyrimidinone (Compound 44)

(R₃=H, q=1, n=1, r=0, R₁=BOC) from 5g (method A)
¹H-NMR (CDCl₃): 1.40 (m, 18H, 2t.Bu); 3.05–3.15 (m, 1H, H-2'a or H-2'b); 3.45–3.55 (m, 1H-2'a or H-2'b); 3.75–4.00 (m, 5H, 2CH₂N and H-5'a or H-5'b); 4.25–4.50 (m, 5H, 2CH₂Ph and H-5'a or H-5'b); 5.25–5.30 (m, 1H, H-4'); 6.15–6.20 (m, 1H, H-1'), 7.10–7.35 (m, 11H, H arom. and H-5); 7.90–7.95 (m, 1H, H-6).

(±)-4-[5-[6-(N'-tert-Butoxycarbonyl-N'-phenylmethylamino)-N-tert-butoxycarbonyl-hexylamino]-pentanoylamino]-1-[2-[5-[6-(N'-tert-butoxycarbonyl-N'-phenylmethyl-amino)-N-tert-butoxycarbonyl-hexylamino]-pentanoyloxymethyl]-1,3-oxathiolan-5-yl]-2(1H)-pyrimidinone (Compound 45)

(R₃=H, q=1, n=6, r=1, m=4, R₁=R₂=BOC) from 10e (method A) which was directly used in the subsequent reaction.

(±)-4-[6-[3-(N'-tert-Butoxycarbonyl-N'-phenylmethylamino)-N-tert-butoxycarbonyl-propylamino]-hexanoylamino]-1-[2-[6-[3-(N'-tert-butoxycarbonyl-N'-phenylmethyl-amino)-N-tert-butoxycarbonyl-propylamino]-hexanoyloxymethyl]-1,3-oxathiolan-5-yl]-2(1H)-pyrimidinone (Compound 46)

(R₃=H, q=1, n=3, r=1, m=5, R₁=R₂=BOC) from 10f (method A) which was directly used in the subsequent reaction.

(±)-4-[5-[5(N'-tert-Butoxycarbonyl-N'-phenylmethylamino)-N-tert-butoxycarbonyl-pentylamino]-pentanoylamino]-1-[2-[5-[5-(N'-tert-butoxycarbonyl-N'-phenylmethyl-amino)-N-tert-butoxycarbonyl-pentylamino]-pentanoyloxymethyl]-1,3-oxathiolan-5-yl]-2(1H)-pyrimidinone (Compound 47)

(R₃=H, q=1, n=5, r=1, m=4, R₁=R₂=BOC) from 10d (method A) which was directly used in the subsequent reaction.

EXAMPLE 2B
Preparation of the compounds of formula (I) wherein R₁=R₂=H

To a solution of 1 equivalent of a compound of formula (I) wherein R₁ and R₂ are different from H, prepared as described in example 1B, in CH₂Cl₂ 20 equivalents of CF₃COOH were added.

The resultant mixture was kept under stirring at room temperature up to the disappearance of the starting compound by TLC (about 2 hours). After evaporation of the solvent, the residue was washed with hexane and purified by preparative thin layer chromatography.

The following compounds of formula (I) were obtained:
Compounds of formula I-A (±)-4-Amino-1-[2-[6-[5-(phenylmethylamino)pentylamino]-hexanoyloxymethyl]-1,3-oxathiolan-5-yl]-2(1H)-pyrimidinone (Compound 48)

(R₃=H, q=1, n=5, r=1, m=5) from Compound 1.
¹H-NMR (CD₃OD): 1.09–1.67 (m, 12H, 6CH₂); 2.09 (t, 2H, J=7.1 Hz, CH₂CO); 2.62–2.75 (m, 6H, CH₂N); 2.95–3.07 (m, 3H, 2NH and H-2'a or H-2'b); 3.23–3.32 (m, 1H, H-2'a or H-2'b); 3.86 (s, 2H, CH₂Ph); 4.02–4.10 (m, 1H, H-5'a or H-5'b); 2H-5'); 4.25–4.34 (m, 1H, H-5'a or H-5'b); 5.12 (pseudo q, 1H, H-4'); 5.81 (d, 1H, J=7.9 Hz, H-5); 5.96 (pseudo q, 1H, H-1'); 7.08–7.18 (m, 5H, H arom.); 7.84 (d, 1H, J=7.9 Hz, H-6).

(±)-4-Amino-1-[2-[5-[6-(phenylmethylamino)hexylamino]-pentanoyloxymethyl]-1,3-oxathiolan-5-yl]-2(1H)-pyrimidinone (Compound 49)

(R₃=H, q=1, n=6, r=1, m=4) from Compound 20

(±)-4-Amino-1-[2-[5-[5-(phenylmethylamino)pentylamino]-pentanoyloxymethyl]-1,3-oxathiolan-5-yl]-2(1H)-pyrimidinone (Compound 50)

(R₃=H, q=1, n=5, r=1, m=4) from Compound 15

(±)-4-Amino-1-[2-[6-[6-(phenylmethylamino)hexylamino]-hexanoyloxymethyl]-1,3-oxathiolan-5-yl]-2(1H)-pyrimidinone (Compound 51)

(R₃=H, q=1, n=6, r=1, m=5) from Compound 3
¹H-NMR (CD₃OD): 1.21–1.89 (m, 14H, 7CH₂); 2.31 (t, 2H, J=6.9 Hz, CH₂CO); 2.74–2.86 (m, 6H, 3CH₂N); 3.05–3.10 (m, 1H, H-2'a or H-2'b), 3.38–3.47 (m, 1H, H-2'a or H-2'b); 3.66–3.89 (m, 2H, 2H-5'); 3.97 (s, 2H, CH₂Ph); 5.13 (t, 1H, J=3.2 Hz, H-4'); 6.09 (pseudo d, 1H, H-1'); 7.02–7.27 (m, 6H, H-5 and H arom.); 8.55 (d, 1H, J=7.5 Hz, H-6).

(±)-4-Amino-1-[2-[6-(phenylmethylamino)hexanoyloxymethyl]-1,3-oxathiolan-5-yl]-2(1H)-pyrimidinone (Compound 52)

(R₃=H, q=1, n=5, r=0) from Compound 4

(±)-4-Amino-1-[2-[6-[(3trifluorophenyl)methylamino]-hexanoyloxymethyl]-1,3-oxathiolan-5-yl]-2(1H)-pyrimidinone (Compound 53)

(R₃=3-CF₃, q=1, n=5, r=0) from Compound 6
¹H-NMR (CD₃OD): 1.28–1.81 (m, 6H, 3CH₂); 2.42 (t, 2H, J=7.1 Hz, CH₂CO); 3.28–3.64 (m, 4H, CH₂N and 2H-2'); 4.29–4.43 (m, 3H, CH₂Ph and H-5'a or H-5'b); 4.58–4.67 (m, 1H, H-5'a or H-5'b); 5.43–5.46 (m, 1H, H-4'); 6.12 (d, 1H, J=7.8 Hz, H-5); 6.28–6.32 (m, 1H, H-1'); 7.52–7.85 (m, 4H, H arom.); 8.15 (d, 1H, J=7.8 Hz, H-6).

(±)-4-Amino-1-[2-[6-[6-[(2-trifluoromethylphenyl)methylamino]-hexylamino]-hexanoyloxymethyl]-1,3-oxathiolan-5-yl]-2(1H)-pyrimidinone (Compound 54)

($R_3$=2-$CF_3$, q=1, n=6, r=1, m=5) from Compound 8

$^1$H-NMR ($CD_3OD$): 1.19–1.61 (m, 14H, 7$CH_2$); 2.31 (t, 2H, J=7.1 Hz, $CH_2CO$); 2.84–3.25 (m, 7H, 3$CH_2N$ and H-2'a or H-2'b); 3.44–3.52 (m, 1H, H-2'a or H-2'b); 4.24–4.32 (m, 3H, $CH_2Ph$ and H-5'a or H-5'b); 4.46–4.55 (m, 1H, H-5'a or H-5'b); 5.34 (q, 1H, $J_1$=3.3 Hz, $J_2$=5.4 Hz, H-4'); 6.18 (bs, 1H, H-5); 6.20 (m, 1H, H-1'); 7.50–7.75 (m, 4H, H arom.); 7.98 (d, 1H, J=7.7 Hz, H-6).

(±)-4-Amino-1-[2-[6-[(2-trifluorophenyl)methylamino]-hexanoyloxymethyl]-1,3-oxathiolan-5-yl]-2(1H)-pyrimidinone (Compound 55)

($R_3$=2-$CF_3$, q=1, n=5, r=0) from Compound 7

$^1$H-NMR ($CD_3OD$): 1.17–1.73 (m, 6H, 3$CH_2$); 2.32 (t, 2H, J=7.1 Hz, $CH_2CO$); 3.00–3.54 (m, 4H, $CH_2N$ and 2H-2'); 4.24–4.32 (m, 3H, $CH_2Ph$ and H-5'a or H-5'b); 4.47–4.56 (m, 1H, H-5'a or H-5'b); 5.34 (q, 1H, $J_1$=3.4 Hz, $J_2$=5.4 Hz, H-4'); 6.17 (bs, 1H, H-5); 6.20 (pseudo q, 1H, H-1'); 7.49–7.74 (m, 4H, H arom.); 8.04 (d, 1H, J=7.8 Hz, H-6).

Compounds of formula I-B (±)-1-(2-Hydroxymethyl-1,3-oxathiolan-5-yl)-4-[6-[6-phenylmethylamino)hexylamino]-hexanoylamino]-2(1H)-pyrimidinone (Compound 56)

($R_3$=H, q=1, n=6, r=1, m=5) from Compound 25

$^1$H-NMR ($CD_3OD$): 1.18–1.82 (m, 14H, 7$CH_2$); 2.24–2.55 (m, 2H, $CH_2CO$); 2.82–2.98 (m, 6H, 3$CH_2N$); 3.10–3.22 (m, 1H, H-2'a or H-2'b); 4.09 (s, 2H, $CH_2Ph$); 4.33–4.39 (m, 1H, H-5'a or H-5'b); 4.51–4.60 (m, 1H, H-5'a or H-5'b); 5.38 (pseudo d, 1H, H-4'); 6.20 (pseudo d, 1H, H-1'); 7.14–7.40 (m, 6H, H-5 and H arom.); 8.22 (d, 1H, J=7.5 Hz, H-6).

(±)-1-(2-Hydroxymethyl-1,3-oxathiolan-5-yl)-4-[6-[5-(phenylmethylamino)pentylamino]-hexanoylamino]-2(1H)-pyrimidinone (Compound 57)

($R_3$=H, q=1, n=5, r=1, m=5) from Compound 23

Rf=0.30 ($CH_2Cl_2$:$CH_3OH$=8:2)

$^1$H-NMR ($CD_3OD$): 1.20–1.61 (m, 12H, 6$CH_2$); 2.30 (t, 2H, J=7.1 Hz, $CH_2CO$); 2.73–2.86 (m, 6H, 3$CH_2N$); 3.03–3.10 (m, 3H, 2NH and H-2'a or H-2'b); 3.37–3.46 (m, 1H, H-2'a or H-2'b); 3.66–3.86 (m, 2H, 2H-5'); 3.97 (s, 2H, $CH_2Ph$); 5.12 (t, 1H, J=3.2 Hz, H-4'); 6.08 (pseudo q, 1H, H-1'), 7.00 (d, 1H, J=3.2 Hz, H-5); 7.19–7.29 (m, 5H, H arom.); 8.53 (d, 1H, J=7.5 Hz, H-6).

(±)-1-(2-Hydroxymethyl-1,3-oxathiolan-5-yl)-4-[5-[6-(phenylmethylamino)hexylamino]-pentanoylamino]-2(1H)-pyrimidinone (Compound 58)

($R_3$=H, q=1, n=6, r=1, m=4) from Compound 32

Rf=0.1 ($CH_2Cl_2$:$CH_3OH$=9:1)

(±)-1-(2-Hydroxymethyl-1,3-oxathiolan-5-yl)-4-[6-[3-(phenylmethylamino)propylamino]-hexanoylamino]-2(1H)-pyrimidinone (Compound 59)

($R_3$=H, q=1, n=3, r=1, m=5) from Compound 33

$^1$H-NMR ($CD_3OD$): 1.30–1.80 (m, 35H, 4$CH_2$); 2.40–2.48 (m, 2H, 2$CH_2CO$); 2.60–2.74 (m, 6H, 3$CH_2N$); 3.19–3.66 (m, 2H, 2H-2'); 3.74 (bs, 2H, $CH_2Ph$); 3.86–4.07 (m, 2H, 2H-5'); 5.31–5.35 (m, 1H, H-4'); 6.27–6.31 (m, 1H, H-1'); 7.20–7.35 (m, 5H, H arom.); 7.42 (d, 1H, J=7.5 Hz, H-5); 8.57 (d, 1H, J=7.5 Hz, H-6).

(±)-1-(2-Hydroxymethyl-1,3-oxathiolan-5-yl)-4-[5-[5-(phenylmethylamino)pentylamino]-pentanoylamino]-2(1H)-pyrimidinone (Compound 60)

($R_3$=H, q=1, n=5, r=1, m=4) from Compound 34

(±)-1-(2Hydroxymethyl-1,3-oxathiolan-5-yl)-4-[6-[4-(phenylmethylamino)butylamino]-hexanoylamino]-2(1H)-pyrimidinone (Compound 61)

($R_3$=H, q=1, n=4, r=1, m=5) from Compound 24

$^1$H-NMR ($CD_3OD$): 1.25–1.85 (m, 10H, 5$CH_2$); 2.40–2.60 (m, 2H, $CH_2CO$); 2.80–3.10 (bs, 7H, 3$CH_2N$ and H-2'a or H-2'b); 3.20–3.30 (m, 1H, H-2'a or H-2'b); 3.60–3.80 (m, 2H, 2H-5'); 4.20 (bs, 2H, $CH_2Ph$); 5.30–5.40 (pseudo t, 1H, H-4'); 6.20–6.35 (m, 1H, H-1'); 7.25 (d, 1H, J=7.5 Hz, H-5); 7.40–7.65 (m, 5H, H arom.); 8.05 (d, 1H, J=7.5 Hz, H-6).

(±)-1-(2-Hydroxymethyl-1,3-oxathiolan-5-yl)4-[6-[6-[(2-trifluoromethylphenyl)-methylamino]-hexylamino]-hexanoylamino]-2(1H)-pyrimidinone (Compound 62)

($R_3$=2-$CF_3$, q=1, n=6, r=1, m=5) from Compound 26

$^1$H-NMR ($CD_3OD$): 1.30–1.57 (m, 14H, 7$CH_2$); 2.35 (t, 2H, J=6.7 Hz, $CH_2CO$); 2.54–3.17 (m, 7H, 3$CH_2N$ and H-2'a or H-2'b); 3.31–3.53 (m, 1H, H-2'a or H-2'b); 3.72–3.94 (m, 2H, 2H-5'); 4.25 (bs, 2H, $CH_2Ph$); 5.19 (t, 1H, J=3.4 Hz, H-4'); 6.15 (q, 1H, $J_1$=2.4 Hz, $J_2$=5.0 Hz, H-1'); 7.17 (bs, 1H, H-5); 7.45–7.70 (m, 4H, H arom.); 8.50 (d, 1H, J=7.5 Hz, H-6).

(±)1-(2-Hydroxymethyl-1,3-oxathiolan-5-yl)-4-[6-(phenylmethylamino)hexanoylamino]-2(1H)-pyrimidinone (Compound 63)

($R_3$=H, q=1, n=5, r=0) from Compound 27

(±)1-(2-Hydroxymethyl-1,3-oxathiolan-5-yl)-4-[6-[(3trifluoromethylphenyl)methyl-amino]-hexanoylamino]-2(1H)-pyrimidinone (Compound 64)

($R_3$=3-$CF_3$, q=1, n=5, r=0) from Compound 28

$^1$H-NMR ($CD_3OD$): 1.22–1.84 (m, 6H, 3$CH_2$); 2.49 (t, 2H, J=7.0 Hz, $CH_2CO$); 3.08–3.53 (m, 2H, $CH_2N$); 3.58–3.73 (m, 1H, H-2'a or H-2'b); 3.87–4.10 (m, 1H, H-2'a or H-2'b); 4.31–4.42 (m, 3H, $CH_2Ph$ and H-5'a or H-5'b); 4.82–4.89 (m, 1H, H-5'a or H-5'b); 5.32–5.35 (t, 1H, H-4'); 6.26–6.30 (m, 1H, H-1'); 7.24–7.85 (m, 5H, H-5, H arom.); 8.63 (d, 1H, J=7.5 Hz, H-6).

(±)1-(2-Hydroxymethyl-1,3-oxathiolan-5-yl)-4-[6-[(2-trifluoromethylphenyl)methyl-amino]-hexanoylamino]-2(1H)-pyrimidinone (Compound 65)

($R_3$=2-$CF_3$, q=1, n=5, r=0) from Compound 29

$^1$H-NMR ($CD_3OD$): 1.17–1.64 (m, 6H, 3$CH_2$); 2.41 (bs, 2H, $CH_2CO$); 3.02–3.19 (m, 3H, $CH_2N$, H-2'a or H-2'b); 3.50–3.54 (m, 1H, H-2'a or H-2'b); 3.76–3.97 (m, 2H, 2H-5'); 4.29 (m, 2H, $CH_2Ph$); 5.23 (t, 1H, J=3.2 Hz, H-4'); 6.19 (bs, 1H, H-1'); 7.49–7.74 (m, 5H, H-5, H arom.); 8.54 (d, 1H, J=6.6 Hz, H-6).

Compounds of formula I-C (±)-4-[6-[5-(Phenylmethylamino)pentylamino]-hexanoylamino]-1-[2-[6-[5-(phenylmethylamino)pentylamino]-hexanoyloxymethyl]-1,3-oxathiolan-5-yl]-2(1H)-pyrimidinone (Compound 66)

($R_3$=H, q=1, n=5, r=1, m=5) from Compound 37

$^1$H-NMR ($CD_3OD$): 1.15–1.55 (m, 24H, 12$CH_2$); 2.06–2.27 (m, 4H, $CH_2CO$); 2.63–2.80 (m, 12H, 6$CH_2N$); 3.00–3.10 (m, 1H, H-2'a or H-2'b); 3.30–3.50 (m, 1H, H-2'a or H-2'b); 3.91 (s, 4H, $CH_2Ph$); 4.13–4.38 (m, 2H, 2H-5'); 5.20 (pseudo q, 1H, H-4'); 6.02 (pseudo d, 1H, H-1'); 7.12–7.23 (m, 11H, H-5, H arom.); 8.09 (d, 1H, J=7.5 Hz, H-6).

(±)-4-[5-[6-(Phenylmethylamino)hexylamino]-pentanoylamino]-1-[2-[5-[6-(phenylmethylamino)hexylamino]-pentanoyloxymethyl]-1,3-oxathiolan-5-yl]-2(1H)-pyrimidinone (Compound 67)

($R_3$=H, q=1, n=6, r=1, m=4) from Compound 45

(±)-4-[6-[6-(Phenylmethylamino)hexylamino]-hexanoylamino]-1-[2-[6-[6-(phenylmethylamino)hexylamino]-hexanoyloxymethyl]-1,3-oxathiolan-5-yl]-2(1H)-pyrimidinone (Compound 68)

($R_3$=H, q=1, n=6, r=1, m=5) from Compound 36

$^1$H-NMR ($CD_3OD$): 1.18–1.88 (m, 28H, 14$CH_2$); 2.26–2.43 (m, 4H, 2$CH_2CO$); 2.84–2.97 (m, 12H, 6$CH_2N$); 3.16–3.20 (m, 1H, H-2'a or H-2'b); 3.51–3.60 (m, 1H, H-2'a or H-2'b); 4.09 (s, 4H, 2CH$_2$Ph); 4.30–4.37 (m, 1H, H-5'a or H-5'b); 4.52–4.61 (m, 1H, H-5'a or H-5'b); 5.38 (pseudo d, 1H, H-4'); 6.21 (pseudo d, 1H, H-1'); 7.32–7.40 (m, 11H, H-5, H arom.); 8.20 (d, 1H, J=7.5 Hz, H-6).

(±)-4-[5-[5-(Phenylmethylamino)pentylamino]-pentanoylamino]-1-[2-[5-[5-(phenylmethylamino) pentylamino]-pentanoyloxymethyl]-1,3-oxathiolan-5-yl]-2 (1H)-pyrimidinone (Compound 69)

($R_3$=H, q=1, n=5, r=1, m=4) from Compound 47
Rf=0.5 (AcOEt)

(±)-4-[6-[3-(Phenylmethylamino)propylamino]-hexanoylamino]1-[2-[6-[3-(phenylmethylamino) propylamino]-hexanoyloxymethyl-]1,3-oxathiolan-5-yl]-2 (1H)-pyrimidinone (Compound 70)

($R_3$=H, q=1, n=3, r=1, m=5) from Compound 46
$^1$H-NMR (CD$_3$OD): 1.25–1.75 (m, 16H, 8CH$_2$); 2.30–2.50 (m, 4H, 2CH$_2$CO); 2.85–3.15 (m, 7H, 3CH$_2$N and H-2'a or H-2'b); 3.50–3.65 (m, 1H, H-2'a or H-2'b); 4.10 (bs, 4H, 2CH$_2$Ph); 4.25–4.60 (m, 2H, 2H-5'); 5.35–5.45 (m, 1H; H-4'); 6.20–6.30 (m, 1H, H-1'); 7.30–7.45 (m, 11H, H-5, H arom.); 8.25 (d, 1H, J=7.5 Hz, H-6).

(±)-4-[6-[4-(Phenylmethylamino)butylamino]-hexanoylamino]-1-[2-[6-[4-(phenylmethylamino) butylamino]-hexanoyloxymethyl]-1,3-oxathiolan-5-yl]-2 (1H)-pyrimidinone (Compound 71)

($R_3$=H, q=1, n=4, r=1, m=5) from Compound 38
$^1$H-NMR (DMSO-d$_6$): 1.10–1.70 (m, 20H, 10CH$_2$); 2.20–2.45 (m, 4H, 2CH$_2$CO); 3.10–3.55 (m, 14H, 6CH$_2$N and 2H-2'); 3.85–4.15 (m, 3H, CH$_2$Ph and H-5'a or H-5'b); 4.25–4.45(m, 1H, H-5'a or H-5'b); 5.25–5.30 (m, 1H, H-4'); 6.05–6.18 (m, 1H, H-1'); 7.10 (d, 1H, J=7.5 Hz, H-5); 7.20–7.45 (m, 10H, H arom.); 8.05 (d, 1H, J=7.5 Hz, H-6).

(±)-4-[6-(Phenylmethylamino)hexanoylamino]-1-[2-[6-(phenylmethylamino)hexanoyloxymethyl]-1,3-oxathiolan-5-yl]-2(1H)-pyrimidinone (Compound 72)

($R_3$=H, q=1, n=5, r=0) from Compound 39
$^1$H-NMR (CD$_3$OD): 1.28–1.72 (m, 6H, 3CH$_2$); 2.40–2.50 (t, 2H, J=6.9 Hz, CH$_2$CO); 2.91–3.28 (m, 3H, CH$_2$N and H-2'a or H-2'b); 3.53–3.69 (m, 1H, H-2'a or H-2'b); 4.19 (bs, 2H, CH$_2$Ph); 4.35–4.70 (m, 2H, 2H-5'); 5.46–5.50 (m, 1H, H-4'); 6.27 (pseudo q, 1H, H-1'); 7.44 (bs, 10H).

(±)-4-[6-[(3-Trifluoromethylphenyl)methylamino]-hexanoylamino]-1-[2-[6-[(3-trifluoromethylphenyl) methylamino]-hexanoyloxymethyl]-1,3-oxathiolan-5-yl]-2 (1H)-pyrimidinone (Compound 73)

($R_3$=3-CF$_3$, q=1, n=5, r=0) from Compound 40
$^1$H-NMR (CD$_3$OD): 1.32–1.73 (m, 12H, 6CH$_2$); 2.44–2.51 (m, 4H, CH$_2$CO); 3.05–3.31 (m, 5H, 2CH$_2$N and H-2'a or H-2'b); 3.61–3.69 (m, 1H, H-2'a or H-2'b); 4.29–4.49 (m, 5H, 2CH$_2$Ph and H-5'a or H-5'b); 4.61–4.70 (m, 1H, H-5'a or H-5'b); 5.48 (m, 1H, H-4'); 6.30 (m, 1H, H-1'); 7.39–7.86 (m, 9H, H arom. and H-5); 8.29 (d, 1H, J=7.5 Hz, H-6).

(±)-4-[6-[6-[(2-Trifluoromethylphenyl)methylamino]-hexylamino]-hexanoylamino]-1-[[2-[6-[6-(2-trifluoromethylphenyl)methylamino]-hexylamino]-hexanoyloxymethyl]-1,3-oxathiolan-5-yl]-2(1H)-pyrimidinone (Compound 74)

($R_3$=2-CF$_3$, q=1, n=6, r=1, m=5) from Compound 42
$^1$H-NMR (CD$_3$OD):1.17–1.58 (m, 28H, 14CH$_2$); 2.25–2.35 (m, 4H, 2CH$_2$CO); 2.80–3.17 (m, 13H, 6CH$_2$N and H-2'a or H-2'b); 3.46–3.55 (m, 1H, H-2'a or H-2'b); 4.25–4.33 (m, 5H, 2CH$_2$Ph and H-5'a or H-5'b); 4.47–4.56 (m, 1H, H-5'a or H-5'b); 5.33 (q, 1H, J$_1$=3.2 Hz, J$_2$=4.8 Hz, H-4'); 6.16 (bs, 1H, H-1'); 7.45–7.70 (m, 9H, H arom. and H-5); 8.16 (d, 1H, J=7.4 Hz, H-6).

(±)-4-[6-[(2-Trifluoromethylphenyl)methylamino]-hexanoylamino]-1-[2-[6-[(2-trifluoromethylphenyl) methylamino]-hexanoyloxymethyl]-1,3-oxathiolan-5-yl]-2 (1H)-pyrimidinone (Compound 75)

($R_3$=2-CF$_3$, q=1, n=5, r=0) from Compound 41
$^1$H-NMR (CD$_3$OD): 1.16–1.65 (m, 12H, 6CH$_2$); 2.28–2.47 (m, 4H, 2CH$_2$CO); 3.04–3.20 (m, 6H, 2CH$_2$N and 2H-2'); 4.28–4.34 (m, 5H, 2CH$_2$Ph and H-5'a or H-5'b); 4.47–4.56 (m, 1H, H-5'a or H-5'b); 5.39 (bs, 1H, H-4'); 6.20 (bs, 1H, H-1'); 7.52–7.73 (m, 9H, H arom. and H-5); 8.38 (bs, 1H, H-6).

Part C—Pharmacologic Activity

EXAMPLE 1C

Anti-HIV activity

The anti-HIV activity of the compounds of formula I was evaluated on the limphocitic human cell line MT4 infected by HIV-1 strain BRU and on fresh human macrophages infected by the macrophage-trophic HIV- 1 PAR strain.

Lymphocytes (MT4 cells)

The cells, infected and treated with the compounds of formula I, were cultured at 37° C. for 7–8 days. Every 3–4 days the culture supernatant was withdrawn and substituted with fresh medium containing or not the compounds of formula I. The anti-HIV activity was evaluated at the end of the experiment as 50% inhibition (IC$_{50}$) of the activity of the viral reverse transcriptase in the supernatant of infected cultures in comparison with the control cultures.

The used methodologies were described in the papers published by Rey M. A. et al. on Biochem. Biophys. Res. Commun. (1984), 121, 126–133 and on Virology (1991), 181, 165–171.

Macrophages

The cells, infected and treated with the compounds of formula I, were cultured at 37° C. for about 1 month. Every 3–4 days the culture supernatant was withdrawn and substituted with fresh medium containing or not the compounds of formula I. The viral reverse-transcriptase activity, determined in the culture supernatant every 3–4 days, was followed up to the end of the experiment by determining the maximum peak of the enzyme expression. In the correspondence of such a peak the anti-HIV activity was evaluated as 50% inhibition (IC$_{50}$) of the enzymatic activity in the supernatant of the infected and treated cultures in comparison with the control ones.

The used methodology was described by Schmidtmayerova H. et al. on Virology (1992), 190, 124–133.

In the following table the data of anti-HIV activity on both the cell lines for some representative compounds of formula I are reported.

| Compound | Lymphocytes IC$_{50}$ ($\mu$M) | Macrophages IC$_{50}$ ($\mu$M) |
|---|---|---|
| 56 | 0.13 | 0.1 |
| 57 | 0.41 | 0.1 |
| 1 | 0.001–0.005 | <10$^{-5}$ |
| 4 | 0.001 | |
| 6 | 0.004 | |
| 7 | 0.001–0.01 | |
| 54 | 0.8 | |
| 48 | 0.15 | |
| 52 | 0.1–1 | |
| 53 | 0.7 | |
| 55 | 0.1 | |
| 9 | 0.001–0.05 | |
| 49 | 0.9 | |
| 10 | 0.01–0.1 | |
| 2 | <0.1 | |
| 8 | 0.1 | |
| BCH-189 | 0.7 | 0.1 |

What is claimed is:

1. A compound of formula

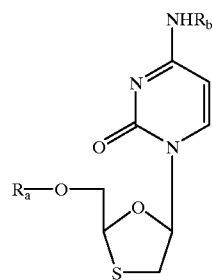

(I)

wherein $R_a$ and $R_b$ are the same or different and are selected from the group consisting of hydrogen, acyl group derived from a lower carboxylic acid or chains of the formula

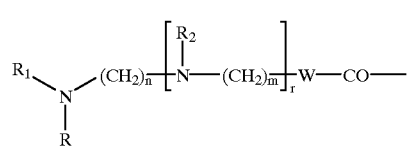

wherein

R is a group of formula

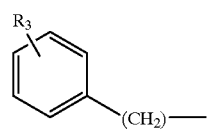

wherein $R_3$ is selected from the group consisting of hydrogen, halogen, trifluoromethyl and $C_1$–$C_3$ alkoxy;

$R_1$ and $R_2$ are the same or different and are selected from the group consisting of hydrogen, phenylalkoxycarbonyl having 1 to 3 carbon atoms in the alkoxy moiety, $C_2$–$C_6$ alkoxycarbonyl and $C_2$–$C_6$ alkylcarbonyl;

W is selected from the group consisting of a single bond, an oxygen atom and a group —CH(Alk)—, wherein Alk is a linear or branched $C_1$–$C_3$ alkyl group;

r is 0 or 1, wherein when r is 0, n is 1 to 6, and when r is 1, n is 2 to 7; and m is 2 to 7, provided that at least one of $R_a$ and $R_b$ is other than a hydrogen atom or an acyl group derived from a lower carboxylic acid.

2. A compound according to claim 1 of formula

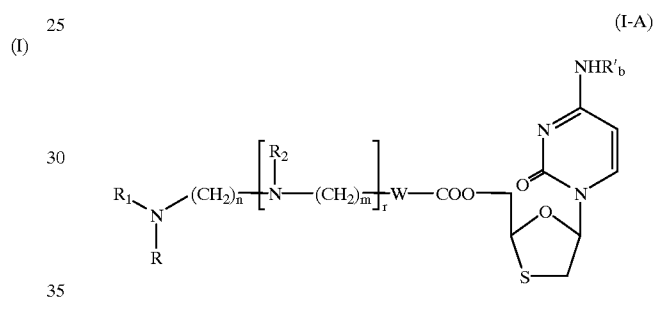

(I-A)

wherein R, $R_1$, $R_2$, W, n, m and r have the meanings reported in claim 1 and $R'_b$ is a hydrogen atom or an acyl group deriving from a lower carboxylic acid.

3. A compound according to claim 1 of formula

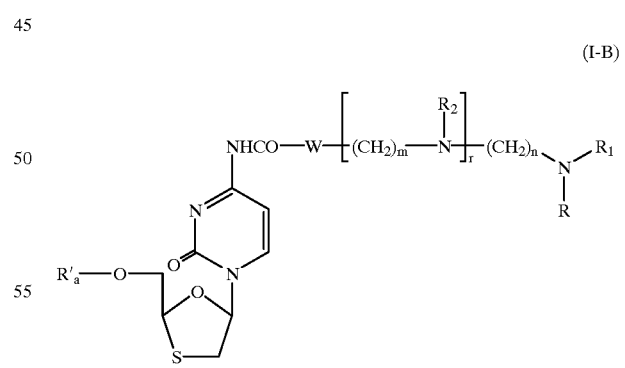

(I-B)

wherein R, $R_1$, $R_2$, W, n, m and r have the meanings reported in claim 1 and $R'_a$ is a hydrogen atom or an acyl group deriving from a lower carboxylic acid.

4. A compound according to claim 1 of formula

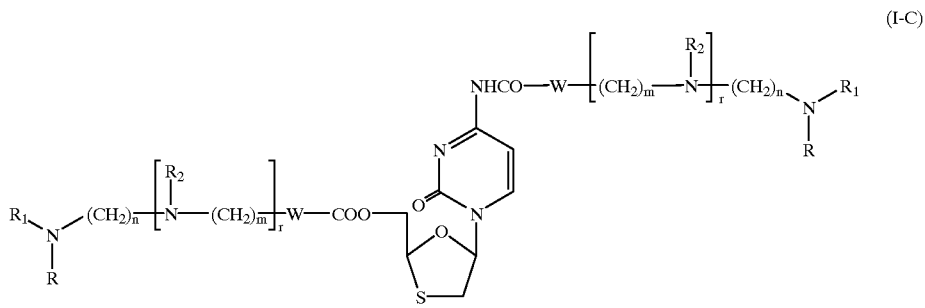

wherein R, $R_1$, $R_2$, W, n, m and r have the meanings reported in claim 1.

5. A compound according to claim 1 having the (2R,5S) configuration of lamivudine.

6. A compound according to claim 1 wherein $R_1$ and $R_2$ are $C_2$–$C_6$ alkoxycarbonyl groups.

7. A compound according to claim 6 wherein $R_1$ and $R_2$ are tert-butoxycarbonyl groups.

8. A compound according to claim 1 wherein W is a single bond and $R_3$ is a hydrogen atom or a trifluoromethyl group.

9. A compound according to claim 8 wherein n is 4 to 6 and m is 4 to 5.

10. A compound according to claim 1 wherein $R_1$ and $R_2$ are other than hydrogen.

11. A process for the preparation of the compounds according to claim 1 comprising the acylation of lamivudine

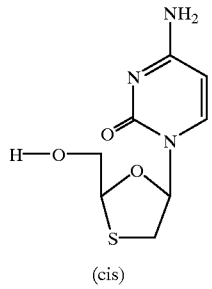

by reaction with a compound of formula

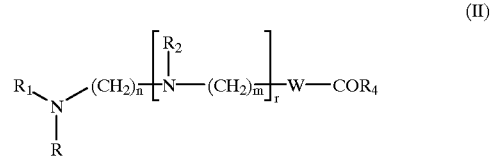

wherein R, $R_1$, $R_2$, n, m and W have the meanings reported in claim 1 and $R_4$ is an OH group or a suitable leaving group when W is different from oxygen or $R_4$ is a suitable leaving group when W is oxygen.

12. A pharmaceutical composition containing one or more compounds according to claim 1 in admixture with a pharmaceutically acceptable carrier.

* * * * *